(12) United States Patent
Rivera et al.

(10) Patent No.: US 8,449,884 B2
(45) Date of Patent: *May 28, 2013

(54) CLOTTING FACTOR-FC CHIMERIC PROTEINS TO TREAT HEMOPHILIA

(75) Inventors: Daniel S. Rivera, Providence, RI (US); Robert T. Peters, W. Roxbury, MA (US); Alan J. Bitonti, Acton, MA (US)

(73) Assignee: Syntonix Pharmaceuticals, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/949,564

(22) Filed: Nov. 18, 2010

(65) Prior Publication Data

US 2011/0182896 A1    Jul. 28, 2011

Related U.S. Application Data

(62) Division of application No. 10/841,819, filed on May 6, 2004, now abandoned.

(60) Provisional application No. 60/468,837, filed on May 6, 2003.

(51) Int. Cl.
*A61K 39/395* (2006.01)

(52) U.S. Cl.
USPC .............. 424/134.1; 514/13.5; 514/14.3

(58) Field of Classification Search
None
See application file for complete search history.

(56) References Cited

U.S. PATENT DOCUMENTS

| | | | |
|---|---|---|---|
| 3,941,763 A | 3/1976 | Sarantakis |
| 4,695,623 A | 9/1987 | Stabinsky |
| 4,784,950 A | 11/1988 | Hagen et al. |
| 4,831,119 A | 5/1989 | Nordfang et al. |
| 4,897,471 A | 1/1990 | Stabinsky |
| 5,077,204 A | 12/1991 | Brake et al. |
| 5,093,246 A | 3/1992 | Cech et al. |
| 5,116,964 A | 5/1992 | Capon et al. |
| 5,162,220 A | 11/1992 | Oshima et al. |
| 5,175,096 A | 12/1992 | Höök et al. |
| 5,180,583 A | 1/1993 | Hedner |
| 5,189,015 A | 2/1993 | Höök et al. |
| 5,234,830 A | 8/1993 | Oshima et al. |
| 5,258,498 A | 11/1993 | Huston et al. |
| 5,428,130 A | 6/1995 | Capon et al. |
| 5,464,933 A | 11/1995 | Bolognesi et al. |
| 5,480,981 A | 1/1996 | Goodwin et al. |
| 5,482,858 A | 1/1996 | Huston et al. |
| 5,579,277 A | 11/1996 | Kelly et al. |
| 5,585,089 A | 12/1996 | Queen et al. |
| 5,591,573 A | 1/1997 | Whalen et al. |
| 5,605,689 A | 2/1997 | Ammann |
| 5,624,821 A | 4/1997 | Winter et al. |
| 5,648,240 A | 7/1997 | Hook et al. |
| 5,723,125 A | 3/1998 | Chang et al. |
| 5,739,277 A | 4/1998 | Presta et al. |
| 5,807,706 A | 9/1998 | Carter et al. |
| 5,808,029 A | 9/1998 | Brockhaus et al. |
| 5,869,046 A | 2/1999 | Presta et al. |
| 5,885,821 A | 3/1999 | Magota et al. |
| 5,910,573 A | 6/1999 | Plückthun et al. |
| 6,013,263 A | 1/2000 | Barney et al. |
| 6,015,881 A | 1/2000 | Kang et al. |
| 6,017,536 A | 1/2000 | Barney et al. |
| 6,030,613 A | 2/2000 | Blumberg et al. |
| 6,060,065 A | 5/2000 | Barney et al. |
| 6,060,613 A | 5/2000 | Hattori et al. |
| 6,068,973 A | 5/2000 | Barney et al. |
| 6,086,875 A | 7/2000 | Blumberg et al. |
| 6,093,799 A | 7/2000 | Li et al. |
| 6,184,344 B1 | 2/2001 | Kent et al. |
| 6,228,983 B1 | 5/2001 | Barney et al. |
| 6,280,994 B1 | 8/2001 | Sheppard et al. |
| 6,281,331 B1 | 8/2001 | Kang et al. |
| 6,310,180 B1 | 10/2001 | Tam |
| 6,310,183 B1 | 10/2001 | Johannessen et al. |
| 6,323,323 B1 | 11/2001 | Sledziewski et al. |
| 6,326,468 B1 | 12/2001 | Canne et al. |
| 6,329,176 B1 | 12/2001 | Wöldike et al. |
| 6,469,136 B1 | 10/2002 | Bray et al. |
| 6,475,491 B1 | 11/2002 | Johnson et al. |
| 6,485,726 B1 | 11/2002 | Blumberg et al. |
| 6,518,013 B1 | 2/2003 | Barney et al. |
| 6,660,843 B1 | 12/2003 | Feige et al. |
| 7,084,109 B2 | 8/2006 | Dennis et al. |
| 7,348,004 B2 | 3/2008 | Peters et al. |
| 7,381,408 B2 | 6/2008 | Mezo et al. |
| 7,385,032 B2 | 6/2008 | Tschopp et al. |
| 7,404,956 B2 | 7/2008 | Peters et al. |
| 7,820,162 B2 | 10/2010 | Mezo et al. |
| 7,862,820 B2 | 1/2011 | Peters et al. |
| 2002/0081664 A1 | 6/2002 | Lo et al. |
| 2002/0106374 A1 | 8/2002 | Olson et al. |
| 2003/0053984 A1 | 3/2003 | Tschopp et al. |
| 2003/0119727 A1 | 6/2003 | Dennis et al. |
| 2003/0180287 A1 | 9/2003 | Gambotz et al. |

(Continued)

FOREIGN PATENT DOCUMENTS

CA    2045869 A1    12/1991
EP    0 325 262 B1    7/1989

(Continued)

OTHER PUBLICATIONS

Bodey et al., Anticancer Research, 1997, 17:1319-1330.*

(Continued)

*Primary Examiner* — Michael Szperka
(74) *Attorney, Agent, or Firm* — Sterne, Kessler, Goldstein & Fox P.L.L.C.

(57) ABSTRACT

The invention relates to a chimeric protein comprising at least one clotting factor and at least a portion of an immunoglobulin constant region. The invention relates to a method of treating a hemostatic disorder comprising administering a therapeutically effective amount of a chimeric protein wherein the chimeric protein comprises at least one clotting factor and at least a portion of an immunoglobulin constant region.

24 Claims, 16 Drawing Sheets

U.S. PATENT DOCUMENTS

| | | |
|---|---|---|
| 2003/0235536 A1 | 12/2003 | Blumberg et al. |
| 2004/0077022 A1 | 4/2004 | Feige et al. |
| 2004/0110929 A1 | 6/2004 | Bjorn et al. |
| 2005/0027109 A1 | 2/2005 | Mezo et al. |
| 2005/0037941 A1 | 2/2005 | Munoz et al. |
| 2005/0037947 A1 | 2/2005 | Bitonti et al. |
| 2005/0147618 A1 | 7/2005 | Rivera et al. |
| 2005/0281829 A1 | 12/2005 | Hehir et al. |
| 2007/0172928 A1 | 7/2007 | Peters et al. |
| 2011/0159540 A1 | 6/2011 | Mezo et al. |
| 2011/0182919 A1 | 7/2011 | Peters et al. |

FOREIGN PATENT DOCUMENTS

| | | |
|---|---|---|
| EP | 0 464 533 A1 | 1/1992 |
| EP | 0 589 577 B1 | 2/1997 |
| EP | 2 077 121 B1 | 2/2011 |
| FR | 2 641 468 A | 7/1990 |
| WO | WO 88/09810 A1 | 12/1988 |
| WO | WO 89/10134 A1 | 2/1989 |
| WO | WO 90/11364 A1 | 10/1990 |
| WO | WO 92/10209 A1 | 6/1992 |
| WO | WO 93/11162 A1 | 6/1993 |
| WO | WO 94/05328 A1 | 3/1994 |
| WO | WO 9405328 A1 * | 3/1994 |
| WO | WO 96/10585 A1 | 4/1996 |
| WO | WO 96/22024 A1 | 7/1996 |
| WO | WO 98/31394 A2 | 7/1998 |
| WO | WO 99/04813 A1 | 2/1999 |
| WO | WO 99/43713 A1 | 9/1999 |
| WO | WO 99/59643 A2 | 11/1999 |
| WO | WO 00/006605 A2 | 2/2000 |
| WO | WO 00/09560 A2 | 2/2000 |
| WO | WO 00/18881 A2 | 4/2000 |
| WO | WO 00/66173 A2 | 11/2000 |
| WO | WO 01/02439 A1 | 1/2001 |
| WO | WO 01/02440 A1 | 1/2001 |
| WO | WO 01/03737 A1 | 1/2001 |
| WO | WO 0102439 A1 * | 1/2001 |
| WO | WO 0102440 A1 * | 1/2001 |
| WO | WO 01/36637 A1 | 5/2001 |
| WO | WO 01/58935 A2 | 8/2001 |
| WO | WO 01/58957 A2 | 8/2001 |
| WO | WO 01/83526 A2 | 11/2001 |
| WO | WO 01/91780 A1 | 12/2001 |
| WO | WO 02/18417 A1 | 3/2002 |
| WO | WO 02/46208 A2 | 6/2002 |
| WO | WO 02/089828 A2 | 11/2002 |
| WO | WO 03/077834 A2 | 9/2003 |
| WO | WO 2004/003176 A2 | 1/2004 |
| WO | WO 2004/004798 A2 | 1/2004 |
| WO | WO 2004/006962 A2 | 1/2004 |
| WO | WO 2004/101740 A2 | 11/2004 |
| WO | WO 2005/001025 A2 | 1/2005 |
| WO | WO 2005/051289 A2 | 6/2005 |

OTHER PUBLICATIONS

US 6,020,459, 02/2000, Barney et al. (withdrawn).

Argos, P., "An Investigation of oligopeptides linking domains in protein tertiary structures and possible candidates for general gene fusion," *J. Mol. Biol.211*:943-958, Elsevier Ltd (1990).

Armour, K.L., et al., "Recombinant human IgG molecules lacking Fcγ receptor I binding and monocyte triggering activities," *Eur. J. Immunol. 29*:2613-2624, Wiley-VCH Verlag GmbH, Weinheim, Fed. Rep. of Germany (1999).

Aruffo, A., et al., "CD44 is the principal cell surface receptor for hyaluronate," *Cell 61*:1303-1313, Cell Press, United States (1990).

Ashkenazi, A., el al., "Protection against endotoxic shock by a tumor necrosis factor receptor immunoadhesin," *Proc. Natl. Acad. Sci. U.S. A. 88*:10535-10539, National Academy of Science, United States (1991).

Bahlmann, F.H., et al., "Erythropoietin: is it more than correcting anaemia?," *Nephrol. Dial. Transplant 19*:20-22, Oxford University Press, UK (2004).

Barré-Sinoussi, F., et al., "Isolation of a T-lymphotropic retrovirus from a patient at risk for acquired immune deficiency syndrome (AIDS)," *Science 220*:868-871, Assoc. for the Advancement of Science, United States (1983).

Baru M. et al., "Liposome-encapsulated DNA Mediated gene transfer and synthesis of human factor IX in mice," *Gene* 161: 143-150, *Elsevier Science B.V.*, Netherlands (1995).

Bennett, B.D., et al., "Extracellular Domain-IgG Fusion Proteins for Three Human Natriuretic Peptide Receptors," *J. Biol. Chem. 226*:23060-230607, American Society for Biochemistry and Molecular Biology, United States (1991).

Brennan, M., et al., "Preparation of Bispecific Antibodies by Chemical Recombination of Monoclonal Immunoglobulin $G_1$ Fragments," *Science 229*:81-83, Assoc. for the Advancement of Science, United States (1985).

Botti, P., et al., "Cyclic Peptides from Linear Unprotected Peptide Precursors through Thiazolidine Formation," *J. Am. Chem. Soc. 118*:10018-10024, American Chemical Society, United States (1996).

Broze, G.J., and Majerus, P.W., et al., "Purification and Properties of Human Coagulation Factor VII," *J. Biol. Chem. 255*:1242-1247, American Society for Biochemistry and Molecular Biology, United States (1980).

Burmeister, W.P., et al., "Crystal structure at 2.2 Å resolution of the MHC-related neonatal Fc Receptor," *Nature 371*:323-324, Nature Publishing Group, UK (1994).

Byrn, R.A., et al., "Biological properties of a CD4 immunoadhesin," *Nature 344*:667-670, Nature Publishing Group, UK (1990).

Capon, D.J., et al., "Designing CD4 immunoadhesins for AIDS therapy," *Nature 337*:525-531, Nature Publishing Group, UK (1989).

Carter, D.C. and Ho, J.X., "Structure of Serum Albumin," *Adv. Prot. Chem. 45*:153-203, Academic Press, United States (1994).

Chalupny, N.J., et al., "T-cell activation molecule 4-1BB binds to extracellular matrix proteins," *Proc. Natl. Acad. Sci. U.S.A. 89*:10360-10364, National Academy of Science, United States (1992).

Chan, D.C. and Kim, P.S., "HIV Entry and Its inhibition," *Cell 93*P:681-684, Cell Press, United States (1998).

Clerc, F.F., et al., "Primary structure control of recombinant proteins using high-performance liquid chromatography, mass spectrometry and microsequencing," *J. Chromatogr. B Biomed. Appl. 662*:245-259, Elsevier, Netherlands (1994).

Cohen, A.J. and Kessler, C.M., "Acquired Inhibitors," *Baillieres Clin. Hematol. 9*:331-354, Bailliere Tindall, UK (1996).

Dagleish, A.G., et al., "The CD4 (T4) antigen is an essential component of the receptor for the AIDS retrovirus," *Nature 312*:763-767, Nature Publishing Group, UK (1984).

Dargaud Y. and Negrier C., "Heamophilia therapies," Expert Opinions on Biological Therapy, 7:651-663, Ashley Publications Ltd., UK (2007).

Davis, L.E., et al., "Preparation and characterization of antibodies with specificity for the amino-terminal tetrapeptide sequence of the platelet-derived connective tissue activating peptide-III," *Biochem. Int. 10*:394-494, Academic Press, Australia (1985).

Dawson, P.E. and Kent, S.B.H., "Synthesis of native Proteins by Chemical Ligation," *Annu. Rev. Biochem. 69*:923-960, Annual Reviews, United States (2000).

De Clercq, E., et al., "New anti-HIV agents and targets," *Med. Res. Rev. 22*:531-565, Wiley, UK (2002).

Duga, S. & Salomon, O., "Factor XI deficiency," *Semin. Thromb. Hemost. 35*:416-25, Thieme, United States, Germany (2009), Abstract.

Dugaiczyk, A., et al., "Nucleotide sequence and the encoded amino acids of human serum albumin mRNA," *Proc. Natl. Acad. Sci. U.S.A. 79*:71-75, National Academy of Science, United States (1982).

Erickson, B.W. and Merrifield, R.B., "Solid-Phase Peptide Synthesis," in *The Proteins, 3rd ed.*, Neurath, H. and Hill, R.L., eds., Springer, New York, N.Y., pp. 255-527 (1976).

Finn, F.M. and Hofmann, K., "The synthesis of peptides by solution methods with emphasis on peptide hormones," eds., in *The Proteins, 3rd ed.*, Neurath, H. and Hill, R.L., eds., Springer, New York, N.Y., pp. 105-237 (1976).

Fischer, K., et al., "The effects of postponing prophylactic treatment on long-term outcome in patients with severe hemophilia," *Blood* 99:2337-2341, American Society for Hematology, United States (2002).

Friend, P.J., et al., "Phase 1 study of an engineered aglycosylated humanized CD3 antibody in renal transplant rejection," *Transplantation* 68:1632-1637, Lippincott Williams & Wilkins, United States (1999).

Frostell-Karlsson, Å., "Biosensor Analysis of the Interaction between Immobilized Human Serum Albumin and Drug Compounds for Prediction of Human Serum Albumin Binding Levels," *J. Med. Chem.* 43:1986-1992, American Chemical Society (2000).

Gallo, R.C., et al., "Frequent Detection and Isolation of cytopathic Retroviruses (HTLV-III) from Patents with AIDS and at Risk for AIDS," *Science* 224: 500-503, Assoc. for the Advancement of Science, United States (1984).

Gascoigne, N.R., et al., "Secretion of a chimeric T-cell receptor-immunoglobulin protein," *Proc. Natl. Acad. Sci. U.S.A.* 84:2936-2940, The National Academy of Science, United States (1987).

Geoghegan, K.F, and Stroh, J.G., "Side-directed conjugation of nonpeptide groups to peptides and proteins via periodate oxidation of a 2-amino alcohol. Application to modification at N-terminal serine," *Bioconjugate Chem.* 3:138-146, American Chemical Society, United States (1992).

Ghetie, V. and Ward, E.S., "Multiple Roles for the Major Histocompatability Complex Class I-Related Receptor FcRn," *Annu. Rev. Immunol.* 18:739-766, Annual Reviews, United States (2000).

Glennie, M.J. and Stevenson, G.T., "Univalent antibodies kill tumor cells in-vitro and in-vivo," *Nature* 295:712-714, Nature Publishing Group, UK (1982).

Growe, G., et al., "Hemophilia and von Willebrand's disease: 2. Management. Association of Hemophilia Clinic Directors of Canada," *Canadian Medical Association Journal* 153(2): 147-157, Canadian Medical Association, Canada (1995).

Hage, D.S. and Tweed, S.A., "Recent advances in chromatographic and electrophoretic methods for the study of drug-protein interactions," *J. Chromatography* 699:499-525, Elsevier, Netherlands (1997).

Hagen, F.S., et al., "Characterization of a cDNA coding for human factor VII," *Proc. Natl. Acad. Sci. U.S.A.* 83:2412-2416, National Academy of Science, United States (1986).

Hammarkjöld, H. and Rekosh, D., "The molecular biology of the human immunodeficiency virus," *Biochim. Biophys. Acta* 989:269-280, Elsevier, Netherlands (1989).

Israel, E.J., et al, "Expression of the neonatal Fc Receptor, FcRn, on human intestinal epithelial cells," *Immunotogy* 92:69-74, Blackwell Sciences, UK (1997).

Jelesarov, I. and Bosshard, H.R., "Thermodynamic Characterization of the Coupled Folding and Association of Heterodimeric Coiled Coils (Leucine Zippers)," *J. Mol. Biol.* 263:344-358, Academic Press, United States (1996).

Johannessen, M., et al., "Comparison of the activated factor VII:C clot analysis and a modified activated factor VII analysis for monitoring factor VII activity in patients treated with recombinant activated factor VII (NovoSeven®)," *Blood Coagul. Fibrinolysis* 11:S159-S164, Lippincott Williams & Wilkins, United States (2000).

Jones, P.T., et al., "Replacing the complementarity-determing regions in a human antibody with those form a mouse," *Nature* 321:522-525, Nature Publishing Group, UK (1986).

Kang, A.S., et al., "Linkage of recognition and repliation functions by assembling combinatorial antibody Fab libraries along phage surfaces," *Proc. Natl. Acad. Sci. U.S.A.* 88:4363-4366, National Academy of Science, United States (1991).

Kasper, C.K., "Hereditary plasma clothing factor disorders and their management," *Haemophilia* 6:13-27, Blackwell Science, UK (2000).

Ketas, T.J., et al., "Human Immunodeficiency Virus Type 1 Attachment, Coreceptor, and Fusion Inhibitors Are Active against both Direct and *trans* Infection of Primary Cells," *J. Virol.* 77:2762-2767, American Society of Microbiology, United States (2003).

Kilby, J.M., et al., "Potent suppression of HIV-1 replication in humans by T-20, a peptide inhibitor of gp41-mediated virus entry," *Nat. Med.* 4:1302-1307, Nature Publishing Group, UK (1998).

Kobayashi, N., et al., "FcRn-mediated transcytosis of immunoglobulin G in human renal proximal tubular epithelial cells," *Am. J. Physiol.* 282:F358-F365, American Physiological Society, United States (2002).

Kostelny, S.A., et al., "Formation of a bispecific antibody by the use of leucine zippers," *J. Immunol.* 148:1547-1553, American Assoc. of Immunologists, United States (1992).

Kürschner, C., et al., "Construction, Purification, and Characterization of New Interferon γ (IFNγ) Inhibitor Proteins," *J. Biol. Chem.* 267:9354-9360, American Society for Biochemistry and Molecular Biology, United States (1992).

Landolfi N.F., "A Chimeric IL-1/Ig Molecule Possesses The Functional Activity of Both Proteins," *J. Immunol.* 146:915-916, American Assoc. of Immunologists, United States (1991).

Lemaitre, M., et al., "Specific antiviral activity of a poly(L-lysine)-conjugated oligodeoxyribonucleotide sequence complementary to vesicular stomatitis virus N protein mRNA initiation site," *Proc. Natl. Acad. Sci. U.S.A.* 84:648-652, National Academy of Science, United States (1987).

Lesslauer, W., et al., "Recombinant soluble tumor necrosis factor receptor proteins protect mice from lipopolysaccharide-induced lethality," *Eur. J. Immunol.* 21:2883-2886, Wiley, Germany (1991).

Letsinger, R.L., et al., "Cholesteryl-conjugated oligonucleotides: synthesis, properties, and activity as inhibitors of replication of human immunodeficiency virus in cell culture." *Proc. Natl. Acad. Sci. U.S.A.* 86:6553-6536, National Academy of Science, United States (1989).

Li, Y.X. et al., "Expression of TPO Mimetic Peptide Chimetic Proteins with Human IgG1 Fc Fragments and Their Biological Characters," *Sheng Wu Gong Cheng Xue Bao,* 18:424-30, Ke xue chu ban she, China (1985).

Linsley, P.S., et al., "Binding of the B cell activation antigen B7 to CD28 costimulates T cell proliferation and interleukin 2 mRNA accumulation," *J. Exp. Med.* 173:721-730, Rockefeller University Press, United States (1991).

Linsley, P.S., et al., "CTLA4 is a Second Receptor for the B Cell Activation Antigen B7," *J. Exp. Med.* 174:561-569, Rockefeller University Press, United States (1991).

Louis, J.M., et al., "Design and Properties of $N_{CCG}$-gp41, a Chimeric gp41 Molecule with Nanomolar HIV Fusion Inhibitory Activity," *J. Biol. Chem.* 276:29485-298489, American Society for Biochemistry and Molecular Biology, United States (2001).

Maddon, P.J., et al., "The T4 Gene Encodes the AIDS Virus Receptor and Is Expressed in the Immune system and the Brain," *Cell* 47:333-348, Cell Press, United States (1986).

Maeda, Y., et al., "Effective renaturation of denatured and reduced immunoglobulin G in vitro without assistance of chaperone," *Protein Eng.* 9:95-100, Oxford University Press, UK (1996).

Marks, J.D., et al., "By-passing immunization: Building high affinity antibodies by chain shuffling," *Biotechnology* 10:779-783, Nature Publishing Group, UK (1992).

Masui, H., et al., "Cytotoxicity against Human Tumor Cells Mediated by the Conjugate of Anti-Epidermal Growth Factor Receptor Monoclonal Antibody to Recombinant Ricin A Chain," *Cancer Res.* 49:3482-3488, American Assoc. for Cancer Research, United States (1989).

McCafferty, J., et al., "Phage antibodies: filamentous phage displaying antibody variable domains," *Nature* 348:552-554, Nature Publishing Group, UK (1990).

McPherson, H., el al., "Synthesis of an RNA-peptide conjugate by orthogonal ligation," *Synlett. S1*:978-980, Georg Thieme Verlag, Germany (1999).

Menegatti, M. and Peyvandi, F., "Factor X deficiency," *Semin. Thromb. Hemost.* 35:407-15, Thieme, United States (Jun. 2009), Abstract.

Merrifield, R.B., "Solid Phase Peptide Synthesis. I. The Synthesis of a Tetrapeptide," *J. Am. Chem. Soc.* 85:2149-2154, American Chemical Society, United States (1963), Abstract.

Merrifield, R.B., "Solid-phase peptide synthesis," in *The Chemistry of Polypeptides*, Katsoyannis, P.G., ed., Plenum Publishing Corporation, New York, N.Y., pp. 335-361(1973).

Muir, T.W., et al., "Expressed protein ligation: A general method for protein engineering," *Proc. Natl. Acad. Sci. U.S.A.* 95:6705-6710, National Academy of Science, United States (1998).

Nilsson, I.M., "The management of Hemophilia Patients with Inhibitors," *Trans. Med. Rev.* 6:285-293, Elsevier, Netherlands (1992).

Nussbaum, O., et al., "Fusogenic Mechanisms of Enveloped-Virus Glycoproteins Analyzed by a Novel Recombinant Vaccinia Virus-Based Assay Quantitating Cell fusion-Dependent Reporter Gene Activation," *J. Virol.* 68:5411-5422, American Society for Microbiology, United States (1994).

Oravcova, J., et al., "Drug-protein binding studies new trends in analytical experimental methodology," *J. Chromatography* 677:1-28, Elsevier, Netherlands (1996).

Package Insert for Proplex T Factor IX complex Heat Treated, revised Nov. 2002, 2 pages (Baxter).

Pedersen, A.H., et al., "Autoactivation of Human Recombinant Coagulation Factor VII," *Biochemistry* 28:9331-9336, American Chemical Society, United States (1989).

Peppel, K., et al., "A Tumor Necrosis Factor (TNF) Receptor-IgG Heavy Chain Chimeric Protein as a Bivalent Antagonist of TNF Activity," *J. Exp. Med.* 174:1483-1489, Rockefeller Univeristy Press, United States (1991).

Petrini, P., "What factors should influence the dosage and interval of prophylactic treatment in patients with severe haemophilia A and B?," *Hemophilia* 7:99-102, Wiley, UK (2001).

Pipe, S., "Antihemophilic factor (recombinant) plasma/albumin-free method for the management and prevention of bleeding episodes in patients with hemophilia A," *Biologies* 3:117-25, Dove Medical Press (NZ), New Zealand (2009).

Pontikaki, I. et al., "Side effects of anti-TNF α therapy in juvenile idiopathic arthritis," *Reumatismo* 58:31-38, Longanesi (2006).

Rahimipour, S., et al., "Design, synthesis, and evaluation of a long-acting, potent analogue of gonadotropin-releasing hormone," *J. Med. Chem.* 44:3654-3652, American Chemical Society (2001).

Ridgway, J. and Gorman, C., "Expression and Activity of IgE Receptor Alpha Chain-IgG Chimeric Molecules," *J. Cell. Biol.* 115, Abstract No. 1448, Rockefeller University Press (1991).

Root, M.J., et al., "Protein Design of an HIV-1 Entry Inhibitor," *Science* 291:884-888, Association for the Advancement of Science, United States (2001).

Rossi, J.J., "Making ribozymes work in cells," *Curr. Biol.* 4:469-471, Elsevier, Netherlands (1994).

Routledge, E.G., et al., "The effect of aglycosylation on the immunogenicity of a humanized therapeutic CD3 monolconal antibody," *Transplantation* 60:847-853, Lippincott Williams & Wilkins, UK (1995).

Sarin, P.S., et al., "Inhibiton of acquired immunodeficiency syndrome virus by oligodeoxynucleoside methylphosphonates," *Proc. Natl. Acad. Sci. U.S.A.* 85:7448-7451, National Academy of Science, United States (1988).

Sarver, N., et al., "Ribozymes as potential anti-HIV-1 therapeutic agents," *Science* 247:1222-1225, Association for the Advancement of Science, United States (1990).

Seelig, G.F., et al., "Synthetic mimics of juxtaposed amino- and carboxyl-terminal peptide domains of human gamma interferon block ligand binding to human gamma interferon receptor," *J. Biol. Chem.* 1:358-363, American Society for Biochemistry and Molecular Biology, United States (1994).

Severinov, K. and Muir, T.W., "Expressed Protein Ligation, a Novel Method for Studying Protein-Protein Interaction in Transcription," *J. Biol. Chem.* 273:16205-16209, American Society for Biochemistry and Molecular Biology, United States (1998).

Shields, R.L., et al., "High Resolution Mapping of the Binding Site on Human IgG1 for FcγRI, FcγRII, FcγRIII, and FcRn and Design of IgG1 Variants with Improved Binding to the FcγR," *J. Biol. Chem.* 276:6591-6604, American Society for Biochemistry and Molecular Biology, United States (2001).

Solulink Biosciences Bioconjugation, Immbolization & Detection Reagents, Kits and Services Catalog (p. 4), 2005, retrieved Dec. 22, 2005, from http://www.solulink_catalog.pdf.

Stamenkovic, I., etal., "The B Lymphocyte Adhesion Molecule CD22 interacts with Leukocyte Common Antigen CD45RO on T Cells and α2-6 Sialyltransferase, CD75, on B Cells," *Cell* 66:1133-1144, Cell Press, United States (1991).

Stein, C.A., et al., "Physiocochemical properties of phosphorothioate oligodeoxynucleotides," *Nucl. Acids. Res.* 16:3209-3221, Oxford University Press, UK (1988).

Stetsenko, D.A. and Gait, M.J., "Efficient Conjugation of Peptides to Oligonucleotdies by 'Native Ligation'," *J. Organic Chemistry* 65:4900-4908, American Chemical Society, United States (2000).

Stevenson, G.T., et al., "Chimeric Univalent Antibodies for Treating Lymphoid Malignancies," *Med. Oncol. Tumor Pharm.* 1:275-278, Humana Press, United States (1984).

Stevenson, G.T., et al., "Conjugation of Human Fc γ in Closed-Hinge or Open-Hinge Configuration to Fab'γ and Analogous Ligands," *J. Immunol.* 158:2242-2250, American Assoc. of Immunologists, United States (1997).

Story, C.M., et al., "A major histocompatibility complex class I-like fc receptor cloned from human placenta: possible role in transfer of immunoglobulin G from mother to fetus," *J. Exp. Med.* 180:2377-2381, Rockefeller University Press, United States (1994).

Swaminathan, S. and Khanna, N., "Affinity Purification of Recombinant Interferon-α on a Mimetic Ligand Adsorbent," *Protein Expr. Purif.* 15:236-242, Elsevier, Netherlands (1999).

Traunecker, A., et al., "Highly efficient neutralization of HIV with recombinant CD4-immunoglobulin molecules," *Nature* 339:68-70, Nature Publishing Group, UK (1989).

Ueda, T., et al., "Favourable interaction between heavy and light chains arrests the undesirable oligomerization of heavy chains in the refolding of denatured and reduced immunoglobulin G," *Cell Mol. Life Sci.* 53:929-934, Birkhäuser Basel,Switzerland (1997).

Van der Krol, A.R., et al., "Modulation of eukaryotic gene expression by complementary RNA or DNA sequences," *BioTechniques* 6:958-976, Informa Healthcare USA, United States (1988).

Van der Meer, P., et al., "Erythropoietin in cardiovascular diseases," *Eur. J. Heart Fail.* 25:285-291, Oxford Journals, UK 2004).

Van der Meer, P., et al., "Erythropoietin improves left ventricular function and coronary flow in an experimental model of ischemia-reperfusion injury," *Eur. J. Heart Fail.* 6:853-859, Oxford Journals, UK (2004).

Waldmann, T.A., "Albumin Catabolism," in *Albumin Structure, Function and Uses*, Rosenoer, V.M., et al., eds., Pergamon Press, Princeton, NJ, pp. 255-273 (1977).

Ward, E.S., and Ghetie, V., "The effector functions of immunoglobulines: implications for therapy," *Ther. Immunol.* 2:77-94, Blackwell Scientific Publications, UK (1995).

Waterhouse, P., et al., "Combinatorial infection and in vivo recombination: a strategy for making large phage antibody repertoires," *Nucl. Acids. Res.* 21:2265-2266, Oxford University Press, UK (1993).

Watson, S.R., et al., "A Homing Receptor-IgG Chimera as a Probe for Adhesive Ligands of Lymph Node High Endothelial Venules," *J. Cell. Biol.* 110:2221-2229, Rockefeller University Press, United States (1990).

Watson, S.R., et al., "Neutrophil influx into an inflammatory site inhibited by a soluble homing receptor-IgG chimaera," *Nature* 349:164-167, Nature Publishing Group, UK (1991).

Wild, C., et al., "A Synthetic peptide inhibitor of human immunodeficiency virus replication: Correlation between solution structure and viral inhibition," *Proc. Natl. Acad. Sci. U.S.A.* 89:10537-10541, National Academy of Science, United States (1992).

Wild, C.T., et al.,"Peptides corresponding to a predictive alpha-helical domain of human immunodeficiency virus type 1 gp4I are potent inhibitors of virus infection," *Proc. Natl. Acad. Sci. U.S.A.* 91:9770-9774, National Academy of Science, United States (1994).

Wilken, J. and Kent, S.B., "Chemical Protein Synthesis," *Curr. Opin. Biotechnol.* 9:412-426, Current Biology, UK (1988).

Xu, D., et al., "Mimetic ligand-based affinity purification of immune complexes and immunoconjugates," *J. Chromatogr. B Biomed Sci. Appl.* 706:217-229, Elsevier, Netherlands (1998).

Zatsepin, T.S., et al., "Synthesis of peptide-oligonucleotide conjugates with single and multiple peptides attached to 2'-aldehydes through thiazolidine, oxime, and hydrazine linkages," *Bioconjugate Chem.* 13:822-830, American Chemical Society, United States (2002).

Zettmeissl, G., et al., "Expression and Characterization of Human CD4: Immunoglobulin Fusion Proteins," *DNA Cell Biol. USA* 9:347-353, Mary Ann Liebert, United States (1990).

Zhang, L., et al., "Preparation of functionally active cell-permeable peptides by single-step ligation of two peptide molecules," *Proc. Nat. Acad. Sci. U.S.A.* 95:9184-9189, National Academy of Science, United States (1998).

Zheng, X.X., et al., "Administration of Noncytolytic IL-10/Fc in Murine Models of Lipopolysaccharide-Induced Septic Shock and Allogenic Islet Transplantation," *J. Immunol.* 154:5590-5600, Wiley, United States (1995).

Zon, G., "Oligonucleotide analogues as potential chemotherapeutic agents," *Pharm. Res.* 5:539-549, Kluwer Academic/Plenum Publishers, United States (1988).

Advisory Action for U.S. Appl. No. 10/841,250, Peters, R.T., filed May 6, 2004, mailed on Apr. 18, 2007.

Advisory Action for U.S. Appl. No. 10/841,250, Peters, R.T., filed May 6, 2004, mailed on Jul. 12, 2007.

Notice of Appeal and Pre-Appeal Brief Request for Review for U.S. Appl. No. 10/841,250, dated Jul. 25, 2007.

Notice of Panel Decision from Pre-Appeal Brief Review for U.S. Appl. No. 10/841,250, mailed on Aug. 28, 2007, United States Patent Office, Alexandria, Virginia.

Office Action for U.S. Appl. No. 10/841,250, Peters, R.T., filed May, 6, 2004, mailed on Jul. 26, 2006.

Office Action for U.S. Appl. No. 10/841,250, Peters, R.T., filed May, 6, 2004, mailed on Jan. 25, 2007.

Office Action for U.S. Appl. No. 10/841,819, Riviera, D.S., filed May, 6, 2004, mailed on Jul. 27, 2007.

Office Action for U.S. Appl. No. 11/029,003, Peters, R.T., filed Jan. 5, 2005, mailed on Nov. 28, 2006.

Office Action for U.S. Appl. No. 11/029,003, Peters, R.T., filed Jan. 5, 2005, mailed on Aug. 8, 2007.

Reply to Office Action for U.S. Appl. No. 11/029,003, Peters, R.T., filed Jan. 5, 2005, dated May 21, 2007.

Office Action mailed Apr. 1, 2008, for U.S. Appl. No. 10/841,819, inventors Rivera et al., mailed May 6, 2004.

Office Action mailed Jan. 18, 2007, for U.S. Appl. No. 10/842,054, inventors Mezo et al., filed May 6, 2004.

Office Action mailed Jul. 25, 2007, for U.S. Appl. No. 10/842,054, inventors Mezo et al., filed May 6, 2004.

Office Action mailed Mar. 12, 2009, for U.S. Appl. No. 110588,431, inventors Peters et al., filed Oct. 27, 2006.

Office Action mailed Oct. 15, 2009, for U.S. Appl. No. 11/588,431, inventors Peters et al., filed Oct. 27, 2006.

Supplementary European Search Report for European Application No. EP 04 75 1356.9, completed Jul. 17, 2006, European Patent Office, Munich, Germany.

Supplementary European Search Report for European Application No. EP 04 77 5946, completed Nov. 16, 2006, European Patent Office, Munich, Germany.

Esp@cenet Database, Unverified English language abstract for EP0464533 A1, Leander, L., et al., 1 page (1992).

Australian Office Action mailed Nov. 24, 2008, for AU Appl. No. 2004239244, inventors Bitonti et al., filed May 6, 2004.

International Search Report for International Application No. PCT/US04/13939, mailed on Jan. 25, 2005, United States Patent Office, Alexandria, Virginia.

International Search Report for International Application No. PCT/US04/13940, mailed Jul. 29, 2005, United States Patent Office, Alexandria, Virginia.

International Search Report for International Application No. PCT/US04/14064, mailed on Apr. 6, 2006, United States Patent Office, Alexandria, Virginia.

International Search Report for International Application No. PCT/US06/000140, mailed on Jun. 2, 2006, European Patent Office, Rijswijk, Netherlands.

Supplementary European Search Report for European Application No. EP 04 75 1357, completed Apr. 25, 2007, European Patent Office, Munich, Germany.

European Office Action mailed Jun. 20, 2007, for European Application No. 04 775 946.9, applicant Syntonix Pharmaceuticals, Inc., filed May 6, 2004.

European Office Action mailed Apr. 1, 2008, for European Application No. 04 775 946.9, applicant Syntonix Pharmaceuticals, Inc., filed May 6, 2004.

European Office Action mailed Jan. 12, 2009, for European Application No. 04 775 946.9, applicant Syntonix Pharmaceutials, Inc., filed May 6, 2004.

European Office Action mailed Jan. 19, 2010, for European Application No. 04 775 946.9, applicant Syntonix Pharmaceuticals, Inc., filed May 6, 2004.

European Office Action mailed Jan. 14, 2008, for European Application No. 04 751 356.9, application Syntonix Pharmaceuticals, Inc., filed May 6, 2004.

European Office Action mailed Aug. 17, 2009, for European Application No. EP 09 004 646.7,applicant Syntonix Pharmaceuticals, Inc., filed May 6, 2004.

European Office Action mailed Jan. 22, 2008, for European Application No. 04 751 357.7, applicant Syntonix Pharmaceuticals, Inc., filed May 6, 2004.

European Office Action mailed Mar. 20, 2007, for European Application No. 04 751 356.9, applicant Syntonix Pharmaceuticals, Inc., filed May 6, 2004.

European Search Report and Opinion completed May 19, 2009, for European Application No. EP 09 00 4646, filed May 6, 2004, European Patent Office, Munich, Germany.

European Search Report and Opinion mailed Mar. 4, 2010 for European Application No. EP 09 013214, filed May 6, 2004.

International Preliminary Examination Report completed Jun. 7, 2005, for International Application No. PCT/US04/13939, filed May 6, 2004, United States Patent Office, Alexandria, Virginia.

International Preliminary Report on Patentability, issued Nov. 11, 2005, for International Application No. PCT/US2004/013940, filed May 6, 2004, United States Patent Office, Alexandria, Virginia.

International Preliminary Report on Patentability, issued May 8, 2005, for International Application No. PCT/USS2004/014064, filed May 6, 2004, United States Patent Office, Alexandria, Virginia.

Opposition Brief filed May 26, 2010 for U.S. Appl. No. 10/841,819, filed May 6, 2004.

Non-final Office Action mailed May 21, 2010 for U.S. Appl. No. 10/841,819, filed May 6, 2004.

Non-final Office Action mailed Dec. 10, 2009 for U.S. Appl. No. 12/100,183, filed Apr. 9, 2008.

Notice of Opposition filed Jun. 18, 2010 for European Patent No. 1624891 B1, filed May 6, 2004 and grated Aug. 26, 2009.

Esp@cenet Database, Unverified English language abstract for FR 2641468 A, Carosella, et al., 1 page (1990).

Esp@cenet Database, Unverified English language abstract for CA 2045869 A1, Leander, et al., 1 page (1991).

Esp@cenet Database, Unverified English language abstract for WO 00/06605 A2, Kufer, et al., 1 page (2000).

Borvak, J., et al., "Functional Expression of the MHC Class I-related Receptor, FcRn, in Endothelial Cells of Mice," *Internat. Immunol.*, 10(9): 1289-1298, Oxford University Press (1998).

Braverman I., "The Cutaneous Microcirculation: Ultrastructure and Microanatomical Organization," *Microcirculation*, 4(3):329-340, Chapman & Hall (1997).

Burkitt, H.G., et al., "Wheater's Functional History," Chapter 8, Circulatory System, p. 145 to 147,3$^{rd}$. Ed. Churchill Livingstone, Longman Group UK, Limited (1993).

Junghans, R.P., "Finally! The Brambell Receptor (FcRB)," *Immunol. Res.* 16(1):29-57, Humana Press Inc., (1997).

Lo, K.M., et al., "High Level Expression and Secretion of Fc-X Fusion Proteins in Mammalian Cells," *Protein Engineering* 11(6):495-500, Oxford University Press (1998).

Schlachetzke, F., et al., "Expression of the Neonatal Fc Receptor (FcRn) at the Blood-brain Barrier," *J. Nettrochem.* 81:203-206, International Society for Neurochemistry, (2002).

Spiekermann, G.M., et al., "Receptor-mediated Immunoglobulin G Transport Across Mucosal Barriers in Adult Life: Functional Expression of FcRn in the Mammalian Lung," *J. Exp. Med.* 196(3): 303-310, The Rockefeller University Press (2002).

Zbrodowski A., "Blood Supply of Subcutaneous Tissue in the Leg and Its Clinical Application," *Clin. Anat.* 8: 202-207, Wiley-Liss, Inc., (1995).

U.S. Appl. No. 60/364,482, filed Mar. 15, 2002 by Blumberg et al.

Notice of Opposition filed Nov. 9, 2011, for European Patent No. 2077121 B1, filed May 6, 2004 and granted Feb. 9, 2011.

European Search Report and Search Opinion completed Feb. 10, 2011, for European Application No. 10184851, filed May 6, 2004, European Patent Office, Munich, Germany.

Partial European Search Report completed Jul. 4, 2011 for European Application No. 10182902, filed May 6, 2004, European Patent Office, Munich, Germany.

European Search Report and Opinion completed Oct. 21, 2011 for European Application No. 10182901, filed May 6, 2004, European Patent Office, Munich, Germany.

European Search Report and Opinion completed Jun. 29, 2011 for European Application No. 10182902, filed May 6, 2004, European Patent Office, Munich, Germany.

European Office Action mailed Mar. 25, 2011, for European Application No. EP 04775946.9, applicant Syntonix Pharmaceuticals, Inc., filed May 6, 2004.

Summons to Attend Oral Proceedings and Annex to the Communication, issued Oct. 5, 2011 for European Patent No. 1624891 B1, filed May 6, 2004 and granted Aug. 26, 2009.

Written Submission in Preparation to/during Oral Proceedings, filed Jan. 27, 2012 for European Patent No. 1624891 B1, filed May 6, 2004 and granted Aug. 26, 2009.

International Preliminary Report (Chapter II), completed Aug. 7, 2006 on Patentability for Internal Application No. PCT/US2004/014064, filed May 6, 2004.

Summons to Attend Oral Proceedings Pursuant to Rule 115(1) EPC in EP Application No, 04775946.9, dated Jul. 25, 2012, Germany.

Office Action mailed Jun. 28, 2012 in U.S. Appl. No. 12/952,551, Peters et al., filed Nov. 23, 2010.

Notice of Allowance and Fee(s) Due mailed Aug. 16, 2012 in U.S. Appl. No. 12/952,551, Peters et al., filed Nov. 23, 2010.

\* cited by examiner

Fig. 3A ala asn ala phe leu leu glu glu leu arg pro gly ser leu
glu arg glu cys lys glu glu gln cys ser phe glu glu glu
ala arg glu ile phe lys asp ala glu arg thr lys leu phe
trp ile ser tyr ser ser asp gly asp gln cys ala ser ser
pro cys gln asn gly gly ser cys lys asp gln leu leu gln
ser tyr ile cys phe cys leu pro ala phe glu gly arg asn
cys glu thr his lys lys asp asp gln leu ile cys val asn
glu asn gly gly cys glu gln tyr cys ser asp his his thr
gly thr lys arg ser cys arg cys his glu gly tyr ser leu
leu ala asp gly val val ser cys thr pro thr val glu tyr
pro cys gly lys ile pro ile leu glu lys arg asn asn ala
ser lys pro gln gly arg ile val gly gly lys val cys pro
lys gly glu cys pro pro trp gln val leu leu leu val asn
gly ala gln leu cys gly gly thr leu ile asn thr thr ile
trp val val ser ala ala his cys phe asp lys ile lys asn
trp arg asn leu ile ile ala val leu gly glu his asp leu
ser glu his asp gly asp glu gln ser arg arg val val ala
gln val ile ile pro ser thr tyr val pro gly thr thr asn
his asp ile ala leu leu leu arg leu his gln pro val val

Fig. 3A (cont.)

leu thr asp his val val pro leu cys leu pro glu glu arg
thr phe ser glu arg thr leu ala phe val arg phe ser leu
val ser gly trp gly gly gln leu leu asp arg gly ala thr
ala leu glu leu met val leu asn val pro arg leu leu met
thr gln asp cys leu gln gln ser arg lys val gly asp ser
pro asn ile thr glu glu tyr met phe cys ala gly tyr ser
asp gly ser lys asp ser cys lys gly asp ser gly gly gly
pro his ala thr his tyr arg gly thr trp tyr leu thr gly
ile val ser trp gly gly gln gly cys ala thr val gly his
phe gly val tyr thr arg val ser gln tyr ile glu glu trp
leu gln lys leu met arg ser glu pro arg pro gly val leu
leu arg ala pro phe phe pro asp lys thr his thr cys pro
pro cys pro ala pro glu leu leu gly gly pro ser ser val
phe leu phe pro pro lys pro lys asp thr leu met ile ser
arg thr pro glu val val thr cys val val val asp val ser
his glu asp pro glu val lys phe asn trp tyr val val asp
gly val glu val his asn ala lys thr lys pro arg glu glu
gln tyr asn ser thr thr tyr arg val val ser val leu thr
val leu his gln asp trp leu asn gly lys glu tyr tyr lys
cys lys val ser asn lys ala leu pro ala pro ile glu lys

Fig. 3A (cont.)

thr ile ser lys ala ala lys gly gln pro arg glu pro gln
val tyr thr leu pro pro ser arg asp glu leu thr thr lys
asn gln val ser leu thr cys leu val lys gly phe tyr pro
ser asp ile ala val val glu trp glu ser asn gly gln pro
glu asn asn tyr lys thr thr pro val leu asp asp ser asp
gly ser phe phe leu tyr ser lys leu thr val asp lys ser
arg trp gln gln gln gly asn val phe ser cys ser val met
his glu ala leu his asn his tyr thr gln lys lys ser leu
ser leu ser pro gly lys (SEQ ID NO:1)

Fig. 3B phe pro asp lys thr his thr cys pro pro cys pro ala pro
glu leu leu gly gly pro ser ser val phe leu phe pro pro
lys pro lys asp thr leu met ile ser arg thr pro glu val
val thr cys val val val asp val ser his glu asp pro glu
val lys phe asn trp tyr val val asp gly val glu val his
asn ala lys thr lys pro arg glu glu gln tyr asn ser thr
thr tyr arg val val ser val leu thr val leu his gln asp
trp leu asn gly lys glu tyr tyr lys cys lys val ser asn
lys ala leu pro ala pro ile glu lys thr ile ser lys ala
ala lys gly gln pro arg glu pro gln val tyr thr leu pro
pro ser arg asp glu leu thr thr lys asn gln val ser leu
thr cys leu val lys gly phe tyr pro ser asp ile ala val
val glu trp glu ser asn gly gln pro glu asn asn tyr lys
thr thr pro val leu asp asp ser asp gly ser phe phe leu
tyr ser lys leu thr val asp lys ser arg trp gln gln gln
gly asn val phe ser cys ser val met his glu ala leu his
asn his tyr thr gln lys lys ser leu ser leu ser pro gly
lys (SEQ ID NO:2)

Fig. 3C gacaaaactcacacgtgcccgccgtgcccagctccggaactgctgggcggaccgt
cagtcttcctcttccccccaaaacccaaggacaccctcatgatctcccggacccc
tgaggtcacatgcgtggtggtggacgtgagccacgaagaccctgaggtcaagttc
aactggtacgtggacggcgtggaggtgcataatgccaagacaaagccgcgggagg
agcagtacaacagcacgtaccgtgtggtcagcgtcctcaccgtcctgcaccagga
ctggctgaatggcaaggagtacaatgtcaaggtctccaacaaagcccctcccagc
ccccatcgagaaaaccatctccaaagccaagggcagccccgagaaccacaggtg
tacaccctgcccccatcccgggatgagctgaccaagaaccaggtcagcctgacct
gcctggtcaaaggcttctatcccagcgacatcgccgtggagtgggagagcaatgg
gcagccggagaacaactacaagaccacgcctcccgtgttggactccgacggctcc
ttcttcctctacagcaagctcaccgtggacaagagcaggtggcagcaggggaacg
tcttctcatgctccgtgatgcatgaggctctgcacaaccactacacgcagaagag
cctctccctgtctccgggtaaa (SEQ ID NO:3)

Fig. 3D gccaacgcgttcctggaggagctgcggccgggctccctggagagggagtgcaagg
aggagcagtgctccttcgaggaggcccgggagatcttcaaggacgcggagaggac
gaagctgttctggatttcttacagtgatggggaccagtgtgcctcaagtccatgc
cagaatgggggctcctgcaaggaccagctccagtcctatatctgcttctgcctcc
ctgccttcgagggccggaactgtgagacgcacaaggatgaccagctgatctgtgt
gaacgagaacggcggctgtgagcagtactgcagtgaccacacgggcaccaagcgc
tcctgtcggtgccacgaggggtactctctgctggcagacggggtgtcctgcacac
ccacagttgaatatccatgtggaaaaatacctattctagaaaaaagaaatgccag
caaaccccaaggccgaattgtgggggcaaggtgtgccccaaggggagtgtcca
tggcaggtcctgttgttggtgaatggagctcagttgtgtgggggaccctgatca
acaccatctgggtggtctccgcggccactgtttcgacaaaatcaagaactggag
gaacctgatcgcggtgctgggcgagcacgacctcagcgagcacgacggggatgag
cagagccggcgggtggcgcaggtcatcatcccagcacgtacgtcccgggcacca
ccaaccacgacatcgcgctgctccgcctgcaccagcccgtggtcctcactgacca
tgtggtgccctctgcctgcccgaacggacgttctctgagaggacgctggcttc
gtgcgcttctcattggtcagcggctggggccagctgctggaccgtggcgccacgg
ccctggagctcatggtcctcaacgtgccccggctgatgacccaggactgcctgca
gcagtcacggaaggtgggagactccccaaatatcacggagtacatgttctgtgcc
ggctactcggatggcagcaaggactcctgcaaggggacagtggaggcccacatg

Fig. 3D (cont.)

ccacccactaccggggcacgtggtacctgacgggcatcgtcagctggggccaggg ctgcgcaaccgtgggccactttggggtgtacaccagggtctcccagtacatcgag tggctgcaaaagctcatgcgctcagagccacgcccaggagtcctcctgcgagccc catttccgacaaaactcacacgtgcccgccgtgcccagctccggaactgctggg cggaccgtcagtcttcctcttcccccaaaacccaaggacaccctcatgatctcc cggacccctgaggtcacatgcgtggtggtggacgtgagccacgaagaccctgagg tcaagttcaactggtacgtggacggcgtggaggtgcataatgccaagacaaagcc gcgggaggagcagtacaacagcacgtaccgtgtggtcagcgtcctcaccgtcctg caccaggactggctgaatggcaaggagtacaatgtcaaggtctccaacaaagccc ctcccagccccatcgagaaaaccatctccaaagccaagggcagccccgagaac cacaggtgtacaccctgccccatcccgggatgagctgaccaagaaccaggtcag cctgacctgcctggtcaaaggcttctatcccagcgacatcgccgtggagtgggag agcaatgggcagccggagaacaactacaagaccacgcctcccgtgttggactccg acggctccttcttcctctacagcaagctcaccgtggacaagagcaggtggcagca ggggaacgtcttctcatgctccgtgatgcatgaggctctgcacaaccactacacg cagaagagcctctccctgtctccgggtaaa (SEQ ID NO:4)

Intravenous PK of FVIIaFc:Fc in MiniPigs

Fig. 9a

Factor IX -Fc amino acid sequence (signal peptide underlined, propeptide in bold)

```
  1  MQRVNMIMAE  SPGLITICLL  GYLLSAECTV  FLDHENANKI  LNRPKRYNSG
 51  KLEEFVQGNL  ERECMEEKCS  FEEAREVFEN  TERTTEFWKQ  YVDGDQCESN
101  PCLNGGSCKD  DINSYECWCP  FGFEGKNCEL  DVTCNIKNGR  CEQFCKNSAD
151  NKVVCSCTEG  YRLAENQKSC  EPAVPFPCGR  VSVSQTSKLT  RAETVFPDVD
201  YVNSTEAETI  LDNITQSTQS  FNDFTRVVGG  EDAKPGQFPW  QVVLNGKVDA
251  FCGGSIVNEK  WIVTAAHCVE  TGVKITVVAG  EHNIEETEHT  EQKRNVIRII
301  PHHNYNAAIN  KYNHDIALLE  LDEPLVLNSY  VTPICIADKE  YTNIFLKFGS
351  GYVSGWGRVF  HKGRSALVLQ  YLRVPLVDRA  TCLRSTKFTI  YNNMFCAGFH
401  EGGRDSCQGD  SGGPHVTEVE  GTSFLTGIIS  WGEECAMKGK  YGIYTKVSRY
451  VNWIKEKTKL  TEFAGAAAVD  KTHTCPPCPA  PELLGGPSVF  LFPPKPKDTL
501  MISRTPEVTC  VVVDVSHEDP  EVKFNWYVDG  VEVHNAKTKP  REEQYNSTYR
551  VVSVLTVLHQ  DWLNGKEYKC  KVSNKALPAP  IEKTISKAKG  QPREPQVYTL
601  PPSRDELTKN  QVSLTCLVKG  FYPSDIAVEW  ESNGQPENNY  KTTPPVLDSD
651  GSFFLYSKLT  VDKSRWQQGN  VFSCSVMHEA  LHNHYTQKSL  SLSPGK
```

Fig. 9B

Factor IX-Fc nucleotide sequence (signal peptide underlined, propeptide in bold)

```
atgcagcgcgtgaacatgatcatggcagaatcaccaggcctcatcaccatctgccttttaggat
atctactcagtgctgaatgtacagttttcttgatcatgaaaacgccaacaaaattctgaatcg
gccaaagaggtataattcaggtaaattggaagagtttgttcaagggaaccttgagagagaatgt
atggaagaaagtgtagttttgaagaagcacgagaagtttttgaaaacactgaaagaacaactg
aattttggaagcagtatgttgatggagatcagtgtgagtccaatccatgtttaaatggcggcag
ttgcaaggatgacattaattcctatgaatgttggtgtccctttggatttgaaggaagaactgt
gaattagatgtaacatgtaacattaagaatggcagatgcgagcagttttgtaaaaatagtgctg
ataacaaggtggtttgctcctgtactgagggatatcgacttgcagaaaccagaagtcctgtga
accagcagtgccatttccatgtggaagagtttctgtttcacaaacttctaagctcaccgtgct
gagactgttttcctgatgtggactatgtaaattctactgaagctgaaaccatttggataaca
tcactcaaagcacccaatcatttaatgacttcactcgggttgttggtggagaagatgccaaacc
aggtcaattcccttggcaggttgttttgaatggtaaagttgatgcattctgtggaggctctatc
gttaatgaaaaatggattgtaactgctgcccactgtgttgaaactggtgttaaaattacagttg
tcgcaggtgaacataatattgaggagacagaacatacagagcaaaagcgaaatgtgattcgaat
tattcctcaccacaactacaatgcagctattaataagtacaaccatgacattgccttctgaa
ctggacgaaccttagtgctaaacagctacgttacacctatttgcattgctgacaaggaataca
cgaacatcttcctcaaatttggatctggctatgtaagtggctggggaagagtcttccacaagg
gagatcagctttagttcttcagtaccttagagttccacttgttgaccgagccacatgtcttcga
tctacaaagttcaccatctataacaacatgttctgtgctggcttccatgaaggaggtagagatt
catgtcaaggagatagtgggggacccatgttactgaagtggaagggaccagtttcttaactgg
aattattagctggggtgaagagtgtgcaatgaaaggcaaatatggaatatataccaaggtatcc
cggtatgtcaactggattaaggaaaaaacaaagctcactgaattcgccggcgccgctgcggtcg
```

Fig. 9B (cont.)

```
acaaaactcacacatgcccaccgtgcccagcacctgaactcctggggggaccgtcagtcttcct
cttccccaaaacccaaggacaccctcatgatctcccggacccctgaggtcacatgcgtggtg
gtggacgtgagccacgaagaccctgaggtcaagttcaactggtacgtggacggcgtggaggtgc
ataatgccaagacaaagccgcgggaggagcagtacaacagcacgtaccgtgtggtcagcgtcct
caccgtcctgcaccaggactggctgaatggcaaggagtacaagtgcaaggtctccaacaaagcc
ctcccagcccccatcgagaaaaccatctccaaagccaaagggcagccccgagaaccacaggtgt
acaccctgcccccatcccgggatgagctgaccaagaaccaggtcagcctgacctgcctggtcaa
aggcttctatcccagcgacatcgccgtggagtgggagagcaatgggcagccggagaacaactac
aagaccacgcctcccgtgttggactccgacggctccttcttcctctacagcaagctcaccgtgg
acaagagcaggtggcagcaggggaacgtcttctcatgctccgtgatgcatgaggctctgcacaa
ccactacacgcagaagagcctctccctgtctccgggtaaatga
```

CLOTTING FACTOR-FC CHIMERIC PROTEINS TO TREAT HEMOPHILIA

DESCRIPTION OF THE INVENTION

This application is a Divisional Application of U.S. patent application Ser. No. 10/841,819, filed May 6, 2004, which claims priority to U.S. Provisional Appln. No. 60/468,837, filed on May 6, 2003, which is incorporated by reference.

FIELD OF THE INVENTION

The content of the electronically submitted sequence listing in ASCII text file (Name: "2159_2380002SEQIDListing.ascii"; Size: 28,054 bytes; and Date of Creation: Mar. 23, 2012) filed with the application is incorporated herein by reference in its entirety.

BACKGROUND OF THE INVENTION

Hemostatic disorders are characterized by uncontrolled bleeding resulting from the inability or reduced ability to form fibrin clots. Hemostatic disorders can result from a genetic defect or can be acquired as a result of an unrelated medical condition (e.g., cancer and related chemotherapy, autoimmune disease) (Kasper 2000, *Hemophilia* 6 (Supp): 13; Cohen et al. 1996, *Bailiere's Clinical Hematology* 9 (2): 331). Typically, hemostatic disorders result from the deficiency of a specific blood clotting factor. Classic examples of hemostatic disorders include hemophilia A, which results from a deficiency in factor VIII; hemophilia B (Christmas Disease), which results from a deficiency in factor IX; and von Willebrand's disease, which results in a defect in von Willebrand's factor. Von Willebrand factor circulates in association with factor VIII and stabilizes it. It mediates the adherence of platelets to each other and to injured blood vessel walls. Other, less common hemostatic disorders include factor XI deficiency (PTA deficiency), factor XII deficiency, as well as deficiencies or structural abnormalities in fibrinogen, prothrombin, factor V, factor VII, factor X, or factor XIII (Kasper 2000, *Hemophilia* 6 (Supp):13).

Clotting factors act in concert with one another in a coagulation cascade that ultimately results in the formation of a fibrin clot (FIG. 1). These factors can exist in a quiescent state as a proenzyme or zymogen or in an activated enzymatic state when stimulated to form a clot. Stimulation of these factors can occur by two distinct pathways, the intrinsic pathway and the extrinsic pathway. The intrinsic pathway refers to those reactions that lead to clot formation through utilization of factors present only in the plasma. In contrast, the extrinsic pathway refers to those reactions that lead to clot formation from release of membrane bound tissue factor upon vessel endothelium disruption.

Factor VII participates in both pathways cleaving factor X into the activated factor Xa in conjunction with tissue factor in the extrinsic pathway or interacting with factor IXa in the intrinsic pathway. Factor VII acts down stream and independently of factors VIII and IX when acting through the extrinsic pathway, thus bypassing the need for these clotting factors. It is, therefore, an attractive therapeutic candidate for treating hemostatic disorders, especially Hemophilia A and B. (U.S. Pat. No. 6,310,183; WO 01/58935).

Factor VII is a vitamin K-dependent plasma protein synthesized in the liver and secreted into the blood as a single-chain glycoprotein with a molecular weight of 53 kDa (Broze et al. 1980, *J. Biol. Chem.* 255:1242). The factor VII zymogen is converted into an activated form (FVIIa) by proteolytic cleavage at a single site, Arg152-Ile153, resulting in two chains, heavy (254 amino acids) and light (154 amino acids) linked by a single disulfide bond (Hagen et al. 1986, *Proc. Natl. Acad. Sci.* (*USA*) 83:2412). The activated form of factor VII binds to tissue factor, which then converts factor X to factor Xa. Factor Xa is required to convert prothrombin to thrombin, which converts fibrinogen to fibrin as a final stage in forming a fibrin clot.

Factor VII undergoes post-translational modifications, including vitamin K dependent carboxylation resulting in ten γ-carboxyglutamic acid residues in the N-terminal region of the molecule. Other post translational modifications include sugar moiety attachment at two naturally occurring N-linked glycosylation sites at position 145 and 322, respectively, and at two naturally occurring O-linked glycosylation sites at position 52 and 60, respectively (WO 01/58935).

Traditional therapy for hemostatic disorders calls for parenteral replacement of deficient clotting factors such as factor VII, factor VIII or factor IX (see, e.g., U.S. Pat. Nos. 6,310,183 and 4,784,950). Treatment often entails both administering clotting factors to treat acute bleeding episodes as well as administering clotting factors to prophylactically deter the occurrence of future bleeding episodes. Prophylaxis has been found to reduce the risk of developing joint problems and arthritis associated with frequent bleeding episodes (Petrini 2001, *Hemophilia* 7:99; Fischer et al. 2002, *Blood* 99 (7):2337).

Traditional therapies, however, have many associated problems. Currently clotting factors must be administered parenterally in order to attain effective doses because to date non-invasive methods have not been successful in attaining therapeutic levels. Problems associated with parenteral administration include injection site occlusion, pain and infection. Use of an in-line catheter increases the risk of all of these events. Specific problems associated with the parenteral administration of clotting factors to infants and small children include central venous access. Additionally, parenteral administration of clotting factors runs the risk of precipitating a bleeding episode. These problems are particularly relevant when the patient is undergoing regular prophylactic administration of a clotting factor.

Clotting factors such as factor IX and factor VIII must be given frequently and in large doses resulting in the development of inhibitor antibodies against the clotting factor in a significant number of patients (see, e.g., Nilsson 1992, *Transfusion Medicine Review* 6 (4):285; Cohen et al. 1996, *Bailiere's Clinical Hematology* 9 (2):331).

One aspect of the invention provides a safer more effective treatment for hemostatic disorders. Another aspect of the invention provides for increased serum half life and increased bioavailability of therapeutics administered through non-invasive means for the treatment of hemostatic disorders thereby reducing the risk of incurring a bleeding episode, infection and injection site occlusion associated with parenteral administration. Another aspect of the invention provides therapy for hemostatic disorders with reduced risk, compared to current therapies, of developing inhibitor antibodies against the clotting factor. Yet another aspect of the invention provides for a prophylactic treatment of a hemostatic disorder.

The aspects of the invention provide for a chimeric protein comprised of at least one clotting factor and at least a portion of an immunoglobulin constant region, wherein the clotting factor is capable of promoting blood coagulation and/or fibrin clot formation.

Chimeric proteins comprising an Fc portion of an immunoglobulin are known (see, e.g., U.S. Pat. Nos. 6,030,613, 6,086,875, 6,485,726, and PCT Application No. US/02/21335) and while chimeric proteins comprised of mutant clotting factors without clotting activity, and immunoglobulins have been previously described (WO 01/02439), chimeric proteins comprising a clotting factor (i.e., having clotting activity) and at least a portion of an immunoglobulin constant region have not been described. Clotting factor as defined below and used herein refers to any molecule with clotting activity.

SUMMARY OF THE INVENTION

The invention relates to an improved chimeric protein for treating hemostatic disorders. The invention provides a chimeric protein to treat a hemostatic disorder that can be administered parenterally or non-invasively (e.g., via a pulmonary, nasal, or oral route). The invention thus relates to a chimeric protein comprising at least one clotting factor and at least a portion of an immunoglobulin constant region.

The invention relates to a method of treating a hemostatic disorder comprising administering a therapeutically effective amount of a chimeric protein comprising at least one clotting factor and at least a portion of an immunoglobulin constant region.

The invention relates to a method of making a chimeric protein comprising at least one clotting factor and at least a portion of an immunoglobulin constant region; said method comprising transfecting a cell with a DNA construct comprising a first DNA sequence encoding at least one clotting factor operatively linked to a second DNA sequence encoding at least a portion of an immunoglobulin; culturing said cell under conditions such that the chimeric protein is expressed; and isolating said chimeric protein from said cell.

The invention relates to a nucleic acid molecule comprising a sequence encoding at least one clotting factor and at least a portion of an immunoglobulin constant region.

The invention relates to a nucleic acid construct comprising a DNA sequence encoding at least one clotting factor and at least a portion of an immunoglobulin constant region.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 3A is the amino acid sequence of a chimeric protein comprising factor VIIa and an Fc fragment of an immunoglobulin (SEQ ID NO:1).

FIG. 3B is the amino acid sequence of an Fc fragment of an immunoglobulin (SEQ ID NO:2).

FIG. 3C is the nucleic acid sequence of an Fc fragment of an immunoglobulin (SEQ ID NO:3).

FIG. 3D is the nucleic acid sequence of a chimeric protein comprising factor VIIa and an Fc fragment of an immunoglobulin (SEQ ID NO:4).

FIG. 9A is the amino acid sequence of the chimeric protein Factor IX-Fc. Included in the sequence is the signal peptide (underlined) which is cleaved by the cell and the propeptide (bold) which is recognized by the vitamin K-dependent γ carboxylase which modifies the Factor IX to achieve full activity. The sequence is subsequently cleaved by PACE to yield Factor IX-Fc.

FIG. 9B is the nucleic acid sequence of the chimeric protein Factor IX-Fc. Included in the sequence is the signal peptide (underlined) and the propeptide (bold) which is recognized by the vitamin K-dependent γ carboxylase which modifies the Factor IX to achieve full activity. The translated sequence is subsequently cleaved by PACE to yield mature Factor IX-Fc.

SUMMARY OF THE SEQUENCES

Figure 1:
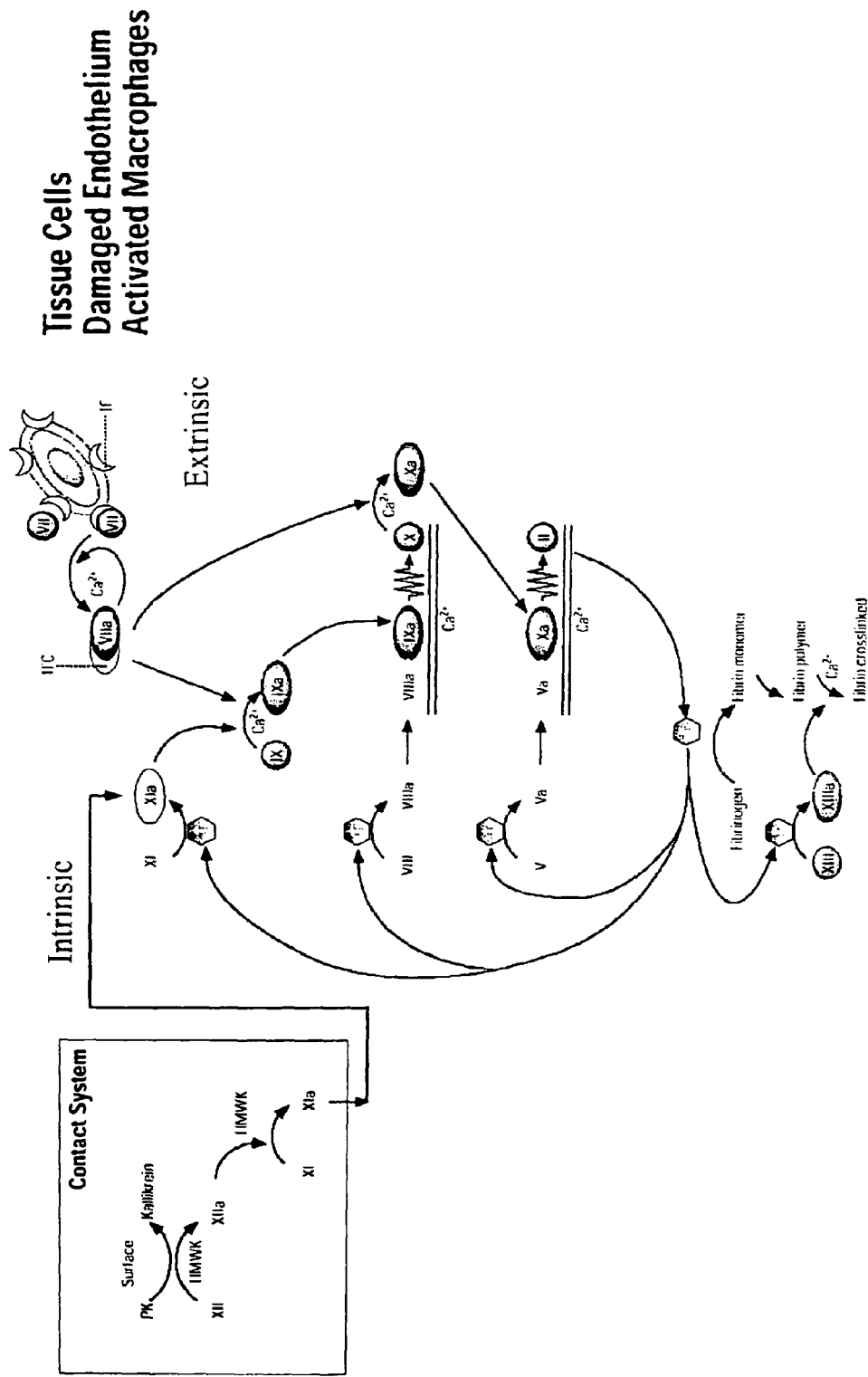
FIG. 1 is a diagram showing the extrinsic and intrinsic pathway of the coagulation cascade.

| Seq ID NO | FIG. | Description |
|---|---|---|
| 1 | 3A | amino acid sequence of a chimeric protein comprising factor VIIA and an IgG FC fragment |
| 2 | 3B | amino acid sequence of an FC fragment of IgG |
| 3 | 3C | nucleic acid sequence corresponding to the amino acid sequence of SEQ ID NO: 2 |
| 4 | 3D | nucleic acid sequence corresponding to the amino acid sequence of SEQ ID NO: 1 |

DESCRIPTION OF THE EMBODIMENTS

A. Definitions

Affinity tag, as used herein, means a molecule attached to a second molecule of interest, capable of interacting with a specific binding partner for the purpose of isolating or identifying said second molecule of interest.

Analogs of, or proteins or peptides or substantially identical to the chimeric proteins of the invention, as used herein, means that a relevant amino acid sequence of a protein or a peptide is at least 70%, 75%, 80%, 85%, 90%, 95%, 97%, 98%, 99%, or 100% identical to a given sequence. By way of example, such sequences may be variants derived from various species, or they may be derived from the given sequence by truncation, deletion, amino acid substitution or addition. Percent identity between two amino acid sequences is determined by standard alignment algorithms such as, for example, Basic Local Alignment Tool (BLAST) described in Altschul et al. (1990) *J. Mol. Biol.*, 215:403-410, the algorithm of Needleman et al. (1970) *J. Mol. Biol.*, 48:444-453; the algorithm of Meyers et al. (1988) *Comput. Appl. Biosci.*, 4:11-17; or Tatusova et al. (1999) *FEMS Microbiol. Lett.*, 174:247-250, etc. Such algorithms are incorporated into the BLASTN, BLASTP and "BLAST 2 Sequences" programs (see www.ncbi.nlm.nih.gov/BLAST). When utilizing such programs, the default parameters can be used. For example, for nucleotide sequences the following settings can be used for "BLAST 2 Sequences": program BLASTN, reward for match 2, penalty for mismatch −2, open gap and extension gap penalties 5 and 2 respectively, gap x_dropoff 50, expect 10, word size 11, filter ON. For amino acid sequences the following settings can be used for "BLAST 2 Sequences": program BLASTP, matrix BLOSUM62, open gap and extension gap penalties 11 and 1 respectively, gap x_dropoff 50, expect 10, word size 3, filter ON.

Bioavailability, as used herein, means the extent and rate at which a substance is absorbed into a living system or is made available at the site of physiological activity.

A chimeric protein, as used herein, refers to any protein comprised of a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric protein can include for example, a protein derived from at least 2 different biological sources. A biological source can include any non-synthetically produced nucleic acid or amino acid sequence (e.g. a genomic or cDNA sequence, a plasmid or viral vector, a native virion or a mutant or analog, as further described herein, of any of the above). A synthetic source can include a protein or nucleic acid sequence produced chemically and not by a biological system (e.g. solid phase synthesis of amino acid sequences). A chimeric protein can also include a protein derived from at least 2 different synthetic sources or a protein derived from at least one biological source and at least one synthetic source.

Clotting factor, as used herein, means any molecule, or analog thereof, naturally occurring or recombinantly produced which prevents or decreases the duration of a bleeding episode in a subject with a hemostatic disorder. In other words, it means any molecule having clotting activity.

Clotting activity, as used herein, means the ability to participate in a cascade of biochemical reactions that culminates in the formation of a fibrin clot and/or reduces the severity, duration or frequency of hemorrhage or bleeding episode.

DNA construct, as used herein, means a DNA molecule, or a clone of such a molecule, either single- or double-stranded that has been modified through human intervention to contain segments of DNA combined in a manner that as a whole would not otherwise exist in nature. DNA constructs contain the information necessary to direct the expression of polypeptides of interest. DNA constructs can include promoters, enhancers and transcription terminators. DNA constructs containing the information necessary to direct the secretion of a polypeptide will also contain at least one secretory signal sequence.

A fragment, as used herein, refers to a peptide or polypeptide comprising an amino acid sequence of at least 2 contiguous amino acid residues, of at least 5 contiguous amino acid residues, of at least 10 contiguous amino acid residues, of at least 15 contiguous amino acid residues, of at least 20 contiguous amino acid residues, of at least 25 contiguous amino acid residues, of at least 40 contiguous amino acid residues, of at least 50 contiguous amino acid residues, of at least 100 contiguous amino acid residues, or of at least 200 contiguous amino acid residues or any deletion or truncation of a protein.

Hemostasis, as used herein, means the stoppage of bleeding or hemorrhage; or the stoppage of blood flow through a blood vessel or body part.

Hemostatic disorder, as used herein, means a genetically inherited or acquired condition characterized by a tendency to hemorrhage, either spontaneously or as a result of trauma, due to an impaired ability or inability to form a fibrin clot.

Linked, as used herein, refers to a first nucleic acid sequence covalently joined to a second nucleic acid sequence. The first nucleic acid sequence can be directly joined or juxtaposed to the second nucleic acid sequence or alternatively an intervening sequence can covalently join the first sequence to the second sequence. Linked as used herein can also refer to a first amino acid sequence covalently joined to a second amino acid sequence. The first amino acid sequence can be directly joined or juxtaposed to the second amino acid sequence or alternatively an intervening sequence can covalently join the first amino acid sequence to the second amino acid sequence. Linked can also refer to a first amino acid sequence non-covalently joined to a second amino acid sequence. Linked as used herein can also refer to a first amino acid sequence covalently joined to a nucleic acid sequence or a small organic or inorganic molecule.

Operatively linked, as used herein, means a first nucleic acid sequence linked to a second nucleic acid sequence such that both sequences are capable of being expressed as a biologically active polypeptide.

A small inorganic molecule, as used herein, means a molecule containing no carbon atoms and being no larger than 50 kD.

A small organic molecule, as used herein, means a molecule containing at least one carbon atom and being no larger than 50 kD.

High stringency, as used herein, includes conditions readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

Moderate stringency, as used herein, include conditions that can be readily determined by those having ordinary skill in the art based on, for example, the length of the DNA. The basic conditions are set forth by Sambrook et al. *Molecular Cloning: A Laboratory Manual*, 2 ed. Vol. 1, pp. 1. 101-104, Cold Spring Harbor Laboratory Press (1989), and include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

Polypeptide, as used herein, refers to a polymer of amino acids and does not refer to a specific length of the product; thus, peptides, oligopeptides, and proteins are included within the definition of polypeptide. This term does not exclude post-expression modifications of the polypeptide, for example, glycosylation, acetylation, phosphorylation, pegylation, addition of a lipid moiety, or the addition of any organic or inorganic molecule. Included within the definition, are for example, polypeptides containing one or more analogs of an amino acid (including, for example, unnatural amino acids) and polypeptides with substituted linkages, as well as other modifications known in the art, both naturally occurring and non-naturally occurring.

Treat, treatment, treating, as used herein, means any of the following: the reduction in severity of a hemostatic disorder; the prophylaxis of one or more symptoms associated with a hemostatic disorder, e.g., a bleeding episode; the reduction in the duration of a disease course of a hemostatic disorder; the amelioration of one or more symptoms associated with a hemostatic disorder; the reduction in duration of a bleeding episode associated with a hemostatic disorder; the reduction in the titer of an inhibitor antibody against a clotting factor; the provision of beneficial effects to a subject with a hemostatic disorder, without necessarily curing the hemostatic disorder.

B. Improved Therapeutics for Hemostatic Disorders

The invention relates generally to improved therapeutics for hemostatic disorders. The invention thus relates to a chimeric protein comprising at least one clotting factor and at least a portion of an immunoglobulin constant region.

The chimeric proteins of the invention have increased stability and other improved properties when compared to known therapeutic agents having clotting activity. They can also be administered parenterally or non-invasively. Accordingly, the invention provides for improved methods for administering therapeutic agents having clotting activity. While clotting factors presently are generally administered subcutaneously, intramuscularly or intravenously, the chimeric proteins of the invention can be administered using less invasive means such as oral administration, nasal administration, or pulmonary administration. In a specific embodiment, the chimeric proteins of the invention are useful in the prophylactic treatment of hemostatic disorders.

The invention also relates generally to improved methods of making therapeutic clotting factors. The invention relates to recombinant methods of producing therapeutic clotting factors with enhanced expression and improved yields. The invention thus relates to methods of making chimeric proteins comprising at least one clotting factor and at least a portion of an immunoglobulin constant region by transfecting a cell with a DNA construct, said construct comprising a DNA sequence encoding at least one clotting factor and a DNA sequence encoding at least a portion of an immunoglobulin constant region; culturing said cell under conditions such that the chimeric protein is expressed by said cell; and isolating said chimeric protein.

C. Chimeric Proteins

The invention relates generally to chimeric proteins comprising at least one clotting factor, at least a portion of an immunoglobulin constant region, and optionally a linker. The clotting factor can be linked covalently, or non-covalently with the portion of an immunoglobulin constant region. The portion of an immunoglobulin constant region will have both an N, or an amino terminus, and a C, or carboxy terminus. In one embodiment, the chimeric protein of the invention may have a clotting factor linked to the N terminus of the portion of an immunoglobulin constant region.

The chimeric protein can optionally comprise at least one linker, thus the clotting factor does not have to be directly linked to the portion of an immunoglobulin constant region. The linker can intervene in between the clotting factor and the portion of an immunoglobulin constant region. The linker can be linked to the N terminus of the portion of an immunoglobulin constant region, or the C terminus of a portion of an immunoglobulin constant region. The linker can be linked to the N terminus of the clotting factor.

The invention thus relates to a chimeric protein comprised of at least one clotting factor (X), optionally, a linker (L), and at least a portion of an immunoglobulin constant region (F). In one embodiment, the invention relates to a chimeric protein comprised of the formula

wherein X is linked at its C terminus to the N terminus of L, and L is linked at its C terminus to the N terminus of F and wherein a is any integer or zero. When a is zero X is directly linked at its C terminus to the N terminus of F. For example, but not as a limitation, a may be 0, 1, 2, 3, 4, 5, 10 or 20.

In one embodiment, the invention relates to a chimeric protein comprising the amino acid sequence of FIG. 3A (SEQ ID NO:1).

The chimeric protein of the invention includes monomers, dimers, as well as higher order multimers. In one embodiment, the chimeric protein is a monomer comprising one clotting factor and one portion of an immunoglobulin constant region. In another embodiment, the chimeric protein is a dimer comprising two clotting factors and two portions of an immunoglobulin. In one embodiment, the two clotting factors are the same. In one embodiment, the two clotting factors are different. In one embodiment, the two portions of an immunoglobulin are the same. In one embodiment, the two portions of an immunoglobulin are different. In another embodiment, the chimeric protein is a monomer/dimer hybrid wherein the chimeric protein has a dimeric aspect in that it is comprised of at least a portion of two immunoglobulin constant region polypeptides and a monomeric aspect in that it is comprised of only one clotting factor linked to one of the two immunoglobulin. The invention thus relates to a chimeric protein comprising a first chain and a second chain, wherein said first chain comprises at least a portion of an immunoglobulin constant region linked to a clotting factor and said second chain comprises at least a portion of an immunoglobulin constant region without a clotting factor linked to it.

Such chimeric proteins may be described using the formulas set forth in Table 1, where I, L, and F are as described above, and where (') indicates a different molecule than without (') and wherein (:) indicates a non-peptide bond

TABLE 1

X-F:F-X
X'-F:F-X
X-L-F:F-X
X-L-F:F-L-X
X'-L-F:F-L-X
X-L'-F:F-L-X
X'-L'-F:F-L-X
F:F-X
F:F-L-X
X-F:F
X-L-F:F
L-F:F-X
X-F:F-L

The skilled artisan will understand additional combinations are possible including the use of additional linkers.

1. Chimeric Protein Variants

Derivatives and analogs of the chimeric proteins of the invention, antibodies against the chimeric proteins of the invention and antibodies against binding partners of the chimeric proteins of the invention are all contemplated, and can be made by altering their amino acid sequences by substitutions, additions, and/or deletions/truncations or by introducing chemical modifications that result in functionally equivalent molecules. It will be understood by one of ordinary skill in the art that certain amino acids in a sequence of any protein may be substituted for other amino acids without adversely affecting the activity of the protein.

Various changes may be made in the amino acid sequences of the chimeric proteins of the invention or DNA sequences encoding therefore without appreciable loss of their biological activity, function, or utility. Derivatives, analogs, or mutants resulting from such changes and the use of such derivatives is within the scope of the present invention. In a specific embodiment, the derivative is functionally active, i.e., capable of exhibiting one or more activities associated with the chimeric proteins of the invention, e.g., clot formation, activation of a clotting factor. Activity can be measured by assays known in the art, e.g., StaCLot FVIIa-rTF assay (Johannessen et al. 2000, *Blood Coagulation and Fibrinolysis* 11:S159) prothrombin time (PT assay) or a APTT assay for factor IX Substitutes for an amino acid within the sequence may be selected from other members of the class to which the amino acid belongs (see Table 2). Furthermore, various amino acids are commonly substituted with neutral amino acids, e.g., alanine, leucine, isoleucine, valine, proline, phenylalanine, tryptophan, and methionine (see, e.g., MacLennan et al. (1998) *Acta Physiol. Scand. Suppl.* 643:55-67; Sasaki et al. (1998) *Adv. Biophys.* 35:1-24).

TABLE 2

| Original Residues | Exemplary Substitutions | Typical Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

2. Clotting Factors

The chimeric proteins of this invention include at least one clotting factor. The clotting factor can include any molecule that has clotting activity or activates a molecule with clotting activity. The clotting factor can be comprised of a polypeptide, a small organic molecule, or a small inorganic molecule. The clotting factor can be a mutated clotting factor or an analog of a clotting factor so long as it maintains at least some clotting activity. The clotting factor can be, as an example, but not as a limitation factor VIII, including B domain deleted factor VIII, factor IX (U.S. Pat. No. 4,994,371), factor XI, factor XII, fibrinogen, prothrombin, factor V, factor VII, factor X, or factor XIII. In one embodiment, the clotting factor is factor VII or factor VIIa. In another embodiment, the clotting factor is a mutated factor VII or VIIa (see, e.g., Persson, et al. 2001, *Proc. Natl. Acad. Sci. USA* 98:13583; U.S. patent application Ser. No. 10/109,498). The clotting factor can be a factor that participates in the extrinsic pathway. The clotting factor can be a factor that participates in the intrinsic pathway. Alternatively, the clotting factor can be a factor that participates in both the extrinsic and intrinsic pathway.

The clotting factor can be a human clotting factor or a non-human clotting factor, e.g., derived from a non-human primate, a pig, or any mammal. The clotting factor can be chimeric clotting factor, e.g., the clotting factor can comprise a portion of a human clotting factor and a portion of a porcine, or any non-human clotting factor or a portion of a first non-human clotting factor and a portion of a second non-human clotting factor.

The clotting factor can be an activated clotting factor. Alternatively the clotting factor can be an inactive form of a clotting factor, e.g., a zymogen. The inactive clotting factor can undergo activation subsequent to being linked to at least a portion of an immunoglobulin constant region. The inactive clotting factor can be activated subsequent to administration to a subject. Alternatively, the inactive clotting factor can be activated prior to administration.

3. Immunoglobulins

The chimeric proteins of this invention include at least a portion of an immunoglobulin constant region. Immunoglobulins are comprised of four protein chains that associate covalently—two heavy chains and two light chains. Each chain is further comprised of one variable region and one constant region. Depending upon the immunoglobulin isotype, the heavy chain constant region is comprised of 3 or 4 constant region domains (e.g., CH1, CH2, CH3, CH4). Some isotypes can also include a hinge region.

The portion of an immunoglobulin constant region can be a portion of an immunoglobulin constant region obtained from any mammal. The portion of an immunoglobulin constant region can include, but is not limited to, a portion of a human immunoglobulin constant region, a non-human primate immunoglobulin constant region, a bovine immunoglobulin constant region, a porcine immunoglobulin constant region, a murine immunoglobulin constant region, an ovine immunoglobulin constant region or a rat immunoglobulin constant region.

The portion of an immunoglobulin constant region can include the entire heavy chain constant region, or a fragment or analog thereof. A heavy chain constant region can comprise a CH1 domain, a CH2 domain, a CH3 domain, and/or a hinge region. A heavy chain constant region can comprise a CH1 domain, a CH2 domain, a CH3 domain, and/or a CH4 domain.

The immunoglobulin can be produced recombinantly or synthetically. The immunoglobulin can be isolated from a cDNA library. The immunoglobulin can be isolated from a phage library (see McCafferty et al. 1990, *Nature* 348:552). The immunoglobulin can be obtained by gene shuffling of known sequences (Mark et al. 1992, *Bio/Technol.* 10:779). The immunoglobulin can be isolated by in vivo recombination (Waterhouse et al. 1993, *Nucl. Acid Res.* 21:2265). The immunoglobulin can be a humanized immunoglobulin (Jones et al. 1986, *Nature* 332:323).

The portion of an immunoglobulin constant region can include a portion of an IgG, an IgA, an IgM, an IgD, an IgE. In one embodiment, the immunoglobulin is an IgG. In another embodiment, the immunoglobulin is IgG1. In yet another embodiment, the immunoglobulin is IgG2.

The portion of an immunoglobulin constant region can include an Fc fragment. An Fc fragment can be comprised of the CH2 and CH3 domains of an immunoglobulin and the hinge region of the immunoglobulin. The Fc fragment can be the Fc fragment of an IgG1, an IgG2, an IgG3 or an IgG4. In one embodiment, the immunoglobulin is an Fc fragment of an IgG1. In one embodiment, the immunoglobulin is an Fc fragment of an IgG2. In another embodiment, the portion of an immunoglobulin constant region is comprised of the amino acid sequence of SEQ ID NO:2 (FIG. 3B) or an analog thereof. In another embodiment, the immunoglobulin is comprised of a protein, or fragment thereof, encoded by the nucleic acid sequence of SEQ ID NO:3 (FIG. 3C).

The portion of an immunoglobulin constant region can include an Fc variant. Fc variant refers to a molecule or sequence that is modified from a native Fc but still comprises a binding site for the salvage receptor, FcRn (WO 97/34631). Native refers to an Fc that has not been modified by a human. WO 96/32478 describes exemplary Fc variants, as well as interaction with the salvage receptor. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, Fc variant comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

In another embodiment, the portion of an immunoglobulin constant region is an neonatal Fc receptor (FcRn) binding partner. An FcRn binding partner is any molecule that can be specifically bound by the FcRn receptor with consequent active transport by the FcRn receptor of the FcRn binding partner. The FcRn receptor has been isolated from several mammalian species including humans. The sequences of the human FcRn, rat FcRn, and mouse FcRn are known (Story et al. 1994, *J. Exp. Med.* 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,030,613 and 6,086,875) including lung and intestinal epithelium (Israel et al. 1997, *Immunology* 92:69) renal proximal tubular epithelium (Kobayashi et al. 2002, *Am. J. Physiol. Renal Physiol.* 282:F358) as well as nasal epithelium, vaginal surfaces, and biliary tree surfaces.

FcRn binding partners of the present invention encompass any molecule that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, *Nature* 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, *Sequences of Proteins of Immunological Interest*, U.S. Department of Public Health, Bethesda, Md.

The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine other amino acids may be substituted for the wildtype amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners.

Certain of the above mutations may confer new functionality upon the FcRn binding partner. For example, one embodiment incorporates N297A, removing a highly conserved N-glycosylation site. The effect of this mutation is to reduce immunogenicity, thereby enhancing circulating half life of the FcRn binding partner, and to render the FcRn binding partner incapable of binding to FcγRI, FcγRIIA, FcγRIIB, and FcγRIIIA, without compromising affinity for FcRn (Routledge et al. 1995, *Transplantation* 60:847; Friend et al. 1999, *Transplantation* 68:1632; Shields et al. 1995, *J. Biol. Chem.* 276:6591). Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" (SEQ ID NO: 32) to the corresponding sequence from IgG2 "PVA" (with one amino acid deletion). It has been shown that FcγRI, FcγRII, and FcγRIII, which mediate various effector functions will not bind to IgG1 when such mutations have been introduced (Ward and Ghetie 1995, *Therapeutic Immunology* 2:77 and Armour et al. 1999, *Eur. J. Immunol.* 29:2613). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, *J. Biol. Chem.* 276:6591).

In one embodiment, the Ran binding partner is a polypeptide including the sequence PKNSSMISNTP (SEQ ID NO: 25) and optionally further including a sequence selected from HQSLGTQ (SEQ ID NO: 26), HQNLSDGK (SEQ ID NO: 27), HQNISDGK (SEQ ID NO: 28), or VISSHLGQ (SEQ ID NO: 29) (U.S. Pat. No. 5,739,277).

Two FcRn receptors can bind a single Fc molecule. Crystallographic data suggest that each FcRn molecule binds a single polypeptide of the Fc homodimer. Linking the FcRn binding partner, e.g., an Fc fragment of an IgG, to a clotting factor thus provides a means of delivering the clotting factor orally or as an aerosol administered nasally, via an ocular route or via a pulmonary route.

The skilled artisan will understand that portions of an immunoglobulin constant region for use in the chimeric protein of the invention can include mutants or analogs thereof, or can include chemically modified immunoglobulin constant regions or fragments thereof (e.g. pegylation) (see, e.g., Aslam and Dent 1998, *Bioconjugation: Protein Coupling Techniques For the Biomedical Sciences Macmilan Reference*, London). In one instance a mutant can provide for enhanced binding of an FcRn binding partner for the FcRn. Also contemplated for use in the chimeric protein of the invention are peptide mimetics of at least a portion of an immunoglobulin constant region, e.g., a peptide mimetic of an Fc fragment or a peptide mimetic of an FcRn binding partner. In one embodiment, the peptide mimetic is identified using phage display (See, e.g., McCafferty et al. 1990, *Nature* 348:552, Kang et al. 1991, *Proc. Natl. Acad. Sci. USA* 88:4363; EP 0 589 877 B1).

4. Optional Linkers

The chimeric protein of the invention can optionally comprise at least one linker molecule. In one embodiment, the linker is comprised of amino acids. The linker can comprise 1-5 amino acids, 1-10 amino acids, 1-20 amino acids, 10-50 amino acids, 50-100 amino acids, 100-200 amino acids. The linker can comprise the sequence G. The linker can comprise the sequence $(GGS)_n$ (SEQ ID NO.: 5). In each instance, n may be an integer, such as 1, 2, 3, 4, 5, 6, 7, 8, 9, or 10. Examples of linkers include, but are not limited to, GGG (SEQ ID NO.: 6), SGGSGGS(SEQ ID NO.: 7), GGSGGSGGSGGSGGG (SEQ ID NO.: 8), and GGSGGSGGSGGSGGSGGS (SEQ ID NO.: 9).

In one embodiment, the linker does not eliminate the clotting activity of the clotting factor. Optionally, the linker enhances the clotting activity of the clotting factor, e.g., by diminishing the effects of steric hindrance and making the clotting factor more accessible to its target binding site, e.g., another factor in the clotting cascade.

D. Nucleic Acid Constructs

The invention relates to a nucleic acid construct comprising a nucleic acid sequence encoding the chimeric proteins of the invention, said nucleic acid sequence comprising a first nucleic acid sequence encoding, for example at least one clotting factor, operatively linked to a second nucleic acid sequence encoding at least a portion of an immunoglobulin constant region. The nucleic acid sequence can also include additional sequences or elements known in the art (e.g. promoters, enhancers, poly A sequences, signal sequence). The nucleic acid sequence can optionally include a sequence encoding a linker placed between the nucleic acid sequence encoding at least one clotting factor and the portion of an immunoglobulin. The nucleic acid sequence can optionally include a linker sequence placed before or after the nucleic acid sequence encoding at least one clotting factor and the portion of an immunoglobulin.

In one embodiment, the nucleic acid construct is comprised of DNA. In another embodiment, the nucleic acid construct is comprised of RNA. The nucleic acid construct can be a vector, e.g., a viral vector or a plasmid. Examples of viral vectors include, but are not limited to adeno virus vector, an adeno associated virus vector or a murine leukemia virus vector. Examples of plasmids include but are not limited to, e.g., pUC and pGEX.

In one embodiment, the nucleic acid construct comprises the nucleic acid sequence of FIG. 3D (SEQ ID NO:4).

Due to the known degeneracy of the genetic code, wherein more than one codon can encode the same amino acid, a DNA sequence can vary from that shown in SEQ ID NOS:3 or 4 and still encode a polypeptide having the amino acid sequence of SEQ ID NOS:2 or 1 respectively. Such variant DNA sequences can result from silent mutations (e.g. occurring during PCR amplification), or can be the product of deliberate mutagenesis of a native sequence. The invention thus provides isolated DNA sequences encoding polypeptides of the invention, selected from: (a) DNA comprising the nucleotide sequence of SEQ ID NO:3 or 4; (b) DNA encoding the polypeptide of SEQ ID NO:1 or 2; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence. The percent identity may be determined by visual inspection and mathematical calculation. Alternatively, the percent identity of two nucleic acid sequences can be determined by comparing sequence information using the GAP computer program, version 6.0 described by Devereux et al. 1984, *Nucl. Acids Res.* 12:387, and available from the University of Wisconsin Genetics Computer Group (UWGCG). The preferred default parameters for the GAP program include: (1) a unary comparison matrix (containing a value of 1 for identities and 0 for non identities) for nucleotides, and the weighted comparison matrix of Gribskov and Burgess 1986, *Nucl. Acids Res.* 14:6745, as described by Schwartz and Dayhoff, eds., 1979, *Atlas of Protein Sequence and Structure*, National Biomedical Research Foundation, pp. 353-358; (2) a penalty of 3.0 for each gap and an additional 0.10 penalty for each symbol in each gap; and (3) no penalty for end gaps. Other programs used by one skilled in the art of sequence comparison may also be used.

E. Synthesis of Chimeric Proteins

Chimeric proteins comprising at least a portion of an immunoglobulin constant region and a clotting factor can be synthesized using techniques well known in the art. For example the chimeric proteins of the invention can be synthesized recombinantly in cells (see, e.g., Sambrook et al. 1989, *Molecular Cloning A Laboratory Manual*, Cold Spring Harbor Laboratory, N.Y. and Ausubel et al. 1989, *Current Protocols in Molecular Biology*, Greene Publishing Associates and Wiley Interscience, N.Y.).

DNA sequences encoding immunoglobulins, or fragments thereof, or clotting factors, or fragments thereof, may be cloned from a variety of genomic or cDNA libraries known in the art. The techniques for isolating such DNA sequences using probe-based methods are conventional techniques and are well known to those skilled in the art. Probes for isolating such DNA sequences may be based on published DNA sequences (see, for example, Hieter et al. 1980, *Cell* 22:197-207). The polymerase chain reaction (PCR) method disclosed by Mullis et al. (U.S. Pat. No. 4,683,195) and Mullis (U.S. Pat. No. 4,683,202) may be used. The choice of library and selection of probes for the isolation of such DNA sequences is within the level of ordinary skill in the art. Alternatively, DNA sequences encoding immunoglobulins, or fragments thereof, or clotting factors can be obtained from vectors known in the art to contain immunoglobulins, or fragments thereof, or clotting factors.

For recombinant production, a polynucleotide sequence encoding the chimeric protein is inserted into an appropriate expression vehicle, i.e., a vector which contains the necessary elements for the transcription and translation of the inserted coding sequence, or in the case of an RNA viral vector, the necessary elements for replication and translation. The nucleic acid encoding the chimeric protein is inserted into the vector in proper reading frame.

In certain embodiments the nucleic acid can also encode for a propeptide clotting factor which is modified by the cell to yield the mature chimeric protein of the invention. In one specific embodiment the propeptide clotting factor is recognized by a vitamin K-dependent γ carboxylase which modifies the propeptide clotting factor to achieve full activity (e.g. factor VII, factor IX, factor X, prothrombin). To yield the mature chimeric protein of the invention, the propeptide sequence is subsequently cleaved by an endoprotease, e.g., paired basic amino acid cleaving enzyme (PACE), or any PACE family member, such as PCSK1-9, including truncated versions thereof, or its yeast equivalent Kex2 from *S. cerevisiae* and truncated versions of Kex2 (see, e.g., U.S. Pat. Nos. 5,077,204; 5,162,220; 5,234,830; 5,885,821; 6,329,176 (Kex2 1-675)).

The expression vehicle is then transfected into a suitable target cell which will express the protein, e.g., a chimeric protein. Transfection techniques known in the art include, but are not limited to, calcium phosphate precipitation (Wigler et al. 1978, *Cell* 14:725) and electroporation (Neumann et al. 1982, *EMBO, J.* 1:841). A variety of host-expression vector systems may be utilized to express the chimeric proteins described herein in eukaryotic cells. In one embodiment, the eukaryotic cell is an animal cell, including mammalian cells (e.g. CHO, BHK, Cos, HeLa cells). When the chimeric protein is expressed in a eukaryotic cell the DNA encoding the chimeric protein may also code for a signal sequence that will permit the chimeric protein to be secreted. One skilled in the art will understand that while the protein is translated the signal sequence is cleaved by the cell to form the mature chimeric protein. Various signal sequences are known in the art e.g., native factor VII signal sequence, native factor IX signal sequence and the mouse Igκ light chain signal sequence. Alternatively, where a signal sequence is not included the chimeric protein can be recovered by lysing the cells.

The chimeric protein of the invention can be synthesized in a transgenic animal, such as a rodent, goat, sheep, pig, or cow. The' term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, *Proc. Natl. Acad. Sci. USA* 82:4438). Methods of producing transgenic animals are known in the art, including transgenics that produce immunoglobulin molecules (Wagner et al. 1981, *Proc. Natl. Acad. Sci. USA* 78:6376; McKnight et al. 1983, *Cell* 34:335; Brinster et al. 1983, *Nature* 306:332; Ritchie et al. 1984, *Nature* 312:517; Baldassarre et al. 2003, *Theriogenology* 59:831; Robl et al. 2003, *Theriogenology* 59:107; Malassagne et al. 2003, Xenotransplantation 10 (3):267).

The expression vectors can encode for tags that permit for easy purification or identification of the recombinantly produced protein. Examples include, but are not limited to, vector pUR278 (Ruther et al. 1983, *EMBO J.* 2:1791) in which the chimeric protein described herein coding sequence may be ligated into the vector in frame with the lac z coding region so that a hybrid protein is produced; pGEX vectors may be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e.g. PreCission Protease™ (Pharmacia, Peapack, N.J.)) for easy removal of the tag after purification.

To increase efficiency of production, the polynucleotide can be designed to encode multiple units of the chimeric protein of the invention separated by enzymatic cleavage sites. The resulting polypeptide can be cleaved (e.g. by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polyproteins and may significantly increase yield of a polypeptide driven by a single promoter.

Vectors used in transformation will usually contain a selectable marker used to identify transformants. In bacterial systems this can include an antibiotic resistance gene such as ampicillin, blasticidin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the dihydrofolate reductase gene (DHFR gene). Another amplifiable marker is the DHFRr cDNA (Simonsen and Levinson 1983, *Proc. Natl. Acad. Sci.* (*USA*) 80:2495). Selectable markers are reviewed by Thilly (*Mammalian Cell Technology*, Butterworth Publishers, Stoneham, Mass.) and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g. heat shock promoters; the promoter for the small subunit of RUBISCO; the promoter for the chlorophyll a/b binding protein) or from plant viruses (e.g. the 35S RNA promoter of CaMV; the coat protein promoter of TMV) may be used; when cloning in mammalian cell systems, promoters derived from the genome of mammalian cells (e.g. metallothionein promoter) or from mammalian viruses (e.g. the adenovirus late promoter; the vaccinia virus 7.5 K promoter, the CMV promoter) may be used; when generating cell lines that contain multiple copies of expression product, SV40-, BPV- and EBV-based vectors may be used with an appropriate selectable marker.

In cases where plant expression vectors are used, the expression of sequences encoding linear or non-cyclized forms of the chimeric proteins of the invention may be driven by any of a number of promoters. For example, viral promoters such as the 35S RNA and 19S RNA promoters of CaMV (Brisson et al. 1984, *Nature* 310:511-514), or the coat protein promoter of TMV (Takamatsu et al. 1987, *EMBO J.* 6:307-311) may be used; alternatively, plant promoters such as the small subunit of RUBISCO (Coruzzi et al. 1984, *EMBO J.* 3:1671-1680; Broglie et al. 1984, *Science* 224:838-843) or heat shock promoters, e.g., soybean hsp17.5-E or hsp17.3-B (Gurley et al. 1986, *Mol. Cell. Biol.* 6:559-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach 1988, *Methods for Plant Molecular Biology*, Academic Press, NY, Section VIII, pp. 421-463; and Grierson & Corey 1988, *Plant Molecular Biology*, 2d Ed., Blackie, London, Ch. 7-9.

In one insect expression system that may be used to produce the chimeric proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e. virus lacking the proteinaceous coat coded for by the polyhedron gene). These recombinant viruses are then used to infect *Spodoptera frugiperda* cells in which the inserted gene is expressed. (see, e.g., Smith et al. 1983, *J. Virol.* 46:584; U.S. Pat. No. 4,215,051). Further examples of this expression system may be found in Ausubel et al., eds 1989, *Current Protocols in Molecular Biology*, Vol. 2, Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. region E1 or E3) will result in a recombinant virus that is viable and capable of expressing a polypeptide peptide in infected hosts (see, e.g., Logan & Shenk 1984, *Proc. Natl. Acad. Sci. (USA)* 81:3655-3659). Alternatively, the vaccinia 7.5 K promoter may be used (see, e.g., Mackett et al. 1982, *Proc. Natl. Acad. Sci. (USA)* 79:7415; Mackett et al. 1984, *J. Virol.* 49:857; Panicali et al. 1982, *Proc. Natl. Acad. Sci.* (USA) 79:4927).

In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. region E1 or E3) will result in a recombinant virus that is viable and capable of expressing a polypeptide in infected hosts (see, e.g., Logan & Shenk 1984, *Proc. Natl. Acad. Sci. (USA)* 81:3655-3659). Alternatively, the vaccinia 7.5 K promoter may be used (see, e.g., Mackett et al. 1982, *Proc. Natl. Acad. Sci. (USA)* 79:7415-7419; Mackett et al. 1984, *J. Virol.* 49:857-864; Panicali et al. 1982, *Proc. Natl. Acad. Sci. (USA)* 79:4927).

Host cells containing DNA constructs of the chimeric protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. In one embodiment, the media contains vitamin K which is necessary for a cellular γ carboxylase to confer activity upon a recombinantly produced clotting factor, e.g., factor VII. Optionally, the media can contain bovine calf serum or fetal calf serum. The growth medium will generally select for cells containing the DNA construct by, for example, drug selection or deficiency in an essential nutrient, which is complemented by the selectable marker on the DNA construct or co-transfected with the DNA construct. Cultured mammalian cells are generally grown in commercially available serum-containing or serum-free media (e.g. MEM, DMEM). Selection of a medium appropriate for the particular cell line used is within the level of ordinary skill in the art.

The recombinantly produced chimeric protein of the invention can be isolated from the culture media using procedures well-established in the art (e.g., affinity chromatography, size exclusion chromatography, ion exchange chromatography). The chimeric protein of the invention can be isolated from the culture media by column chromatography, e.g., a protein A column, or by ion exchange chromatography. When a protein A column or ion exchange column is used to separate the chimeric protein of the invention the chromatographic separation can contribute to the activation of the chimeric protein of the invention, e.g., by converting factor VII to factor VIIa. The culture medium from appropriately grown transformed or transfected host cells is separated from the cell material, and the presence of chimeric proteins is demonstrated. One method of detecting the chimeric proteins, for example, is by the binding of the chimeric proteins or portions of the chimeric proteins to a specific antibody recognizing the chimeric protein of the invention (e.g., an anti-Fc antibody). An anti-chimeric protein antibody may be a monoclonal or polyclonal antibody raised against the chimeric protein in question. For example, the chimeric protein can contain a portion of an immunoglobulin constant region. Antibodies recognizing the constant region of many immunoglobulins are known in the art and are commercially available. An antibody can be used to perform an ELISA or a western blot to detect the presence of the chimeric protein of the invention.

F. Methods of Using Chimeric Proteins

The chimeric proteins of the invention have many uses as will be recognized by one skilled in the art, including, but not limited to methods of treating a subject having a hemostatic disorder and methods of treating a subject in need of a general hemostatic agent.

1. Methods of Treating a Subject Having a Hemostatic Disorder

The invention relates to a method of treating a subject having a hemostatic disorder comprising administering a therapeutically effective amount of at least one chimeric protein, wherein the chimeric protein comprises at least a portion of an immunoglobulin constant region and at least one clotting factor.

The chimeric protein of the invention treats or prevents a hemostatic disorder by promoting the formation of a fibrin clot. The chimeric protein of the invention can activate any member of a coagulation cascade. The clotting factor can be a participant in the extrinsic pathway, the intrinsic pathway or both. In one embodiment, the clotting factor is factor VII or factor VIIa. Factor VIIa can activate factor X which interacts with factor Va to cleave prothrombin to thrombin, which in turn cleaves fibrinogen to fibrin.

a. Conditions that May be Treated

The chimeric protein of the invention can be used to treat any hemostatic disorder. The hemostatic disorders that may be treated by administration of the chimeric protein of the invention include, but are not limited to, hemophilia A, hemophilia B, von Willebrand's disease, factor XI deficiency (PTA deficiency), factor XII deficiency, as well as deficiencies or structural abnormalities in fibrinogen, prothrombin, factor V, factor VII, factor X, or factor XIII.

In one embodiment, the hemostatic disorder is an inherited disorder. In one embodiment, the subject has hemophilia A, and the chimeric protein comprises factor VIII or factor VIIIa. In another embodiment, the subject has hemophilia A and the chimeric protein comprises factor VII or factor VIIa. In another embodiment, the subject has hemophilia B and the chimeric protein comprises factor IX or factor IXa. In another embodiment, the subject has hemophilia B and the chimeric protein comprises factor VII or factor VIIa. In another embodiment, the subject has inhibitory antibodies to factor VIII or factor VIIIa and the chimeric protein comprises factor VII or factor VIIa. In yet another embodiment, the subject has inhibitory antibodies against factor IX or factor IXa and the chimeric protein comprises factor VII or factor VIIa.

The chimeric protein of the invention can be used to prophylactically treat a subject with a hemostatic disorder. The chimeric protein of the invention can be used to treat an acute bleeding episode in a subject with a hemostatic disorder.

In one embodiment, the hemostatic disorder is the result of a deficiency in a clotting factor, e.g., factor IX, factor VIII, factor VII. In another embodiment, the hemostatic disorder can be the result of a defective clotting factor, e.g., von Willebrand's factor.

In another embodiment, the hemostatic disorder can be an acquired disorder. The acquired disorder can result from an underlying secondary disease or condition. The unrelated condition can be, as an example, but not as a limitation, cancer, an auto-immune disease, or pregnancy. The acquired disorder can result from old age or from medication to treat an underlying secondary disorder (e.g. cancer chemotherapy).

2. Methods of Treating a Subject in Need of a General Hemostatic Agent

The invention also relates to methods of treating a subject that does not have a hemostatic disorder or a secondary disease or condition resulting in acquisition of a hemostatic disorder. The invention thus relates to a method of treating a subject in need of a general hemostatic agent comprising administering a therapeutically effective amount of at least one chimeric protein, wherein the chimeric protein comprises at least a portion of an immunoglobulin constant region and at least one clotting factor.

a. Conditions that May be Treated

In one embodiment, the subject in need of a general hemostatic agent is undergoing, or is about to undergo, surgery. The chimeric protein of the invention can be administered prior to, during, or after surgery as a prophylactic. The chimeric protein of the invention can be administered prior to, during, or after surgery to control an acute bleeding episode. The surgery can include, but is not limited to liver transplantation, liver resection, or stem cell transplantation.

The chimeric protein of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

b. Treatment Modalities

The chimeric protein of the invention can be administered intravenously, subcutaneously, intra-muscularly, or via any mucosal surface, e.g., orally, sublingually, buccally, nasally, rectally, vaginally or via pulmonary route. The chimeric protein can be implanted within or linked to a biopolymer solid support that allows for the slow release of the chimeric protein to the site of bleeding or implanted into bandage/dressing.

The dose of the chimeric protein of the invention will vary depending on the subject and upon the particular route of administration used. Dosages can range from 0.1 to 100,000 µg/kg body weight. In one embodiment, the dosing range is 0.1-1,000 µg/kg. The protein can be administered continuously or at specific timed intervals. In vitro assays may be employed to determine optimal dose ranges and/or schedules for administration. In vitro assays that measure clotting factor activity are known in the art, e.g., STA-CLOT VIIa-rTF clotting assay. Additionally, effective doses may be extrapolated from dose-response curves obtained from animal models, e.g., a hemophiliac dog (Mount et al. 2002, *Blood* 99 (8): 2670).

The invention also relates to a pharmaceutical composition comprising a clotting factor, at least a portion of an immunoglobulin constant region and a pharmaceutically acceptable carrier or excipients. Examples of suitable pharmaceutical carriers are described in Remington's Pharmaceutical Sciences by E.W. Martin. Examples of excipients can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g. sorbitol syrup, cellulose derivatives or hydrogenated edible fats), emulsifying agents (lecithin or acacia), non-aqueous vehicles (e.g. almond oil, oily esters, ethyl alcohol, or fractionated vegetable oils), and preservatives (e.g. methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition may take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can be formulated for parenteral administration (i.e. intravenous or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

The pharmaceutical composition can also be formulated for rectal administration as a suppository or retention enema, e.g., containing conventional suppository bases such as cocoa butter or other glycerides.

c. Combination Therapy

In another embodiment, the invention relates to a method of treating a subject with a hemostatic disorder comprising administering a therapeutically effective amount of at least one chimeric protein comprising at least one clotting factor and at least a portion of an immunoglobulin constant region in combination with at least one other clotting factor or agent that promotes hemostasis. Said other clotting factor or agent that promotes hemostasis can be any therapeutic with demonstrated clotting activity. As an example, but not as a limitation, the clotting factor or hemostatic agent can include factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-amino-caproic acid, tranexamic acid.

G. Kits

The invention provides a kit for the diagnosis of a hemostatic disorder. The kit can include a container and a chimeric protein comprising at least one clotting factor and at least a portion of an immunoglobulin constant region. The chimeric protein can be provided in an appropriate buffer or solvent. The buffer can be an aqueous buffer, e.g., PBS or alternatively the chimeric protein can be lyophilized. The kit can also provide instructions for detecting the presence of a clotting factor in a sample, e.g., contacting an aliquot of a sample with the chimeric protein of the invention and detecting the presence of a clot. Detection can include visible detection. The kit can optionally provide an aliquot of blood lacking a known clotting factor.

EXAMPLES

Example 1

Cloning of pcDNA 3.1-Flag-Fc

The sequence for the FLAG peptide (Asp-Tyr-Lys-Asp-Asp-Asp-Asp-Lys) (SEQ ID NO: 22), a common affinity tag used to identify or purify proteins, was cloned into the pcDNA 3.1-Fc plasmid, which contains the mouse Igκ signal sequence followed by the Fc fragment of human IgG1 (amino acids 221-447, EU numbering). The construct was created by overlapping PCR using the following primers:

```
FlagFc-F1:
                                          (SEQ ID NO: 10)
5'-GCTGGCTAGCCACCATGGA-3'

FlagFc-R1:
                                          (SEQ ID NO: 11)
5'-CTTGTCATCGTCGTCCTTGTAGTCGTCA
CCAGTGGAACCTGGAAC-3'

FlagFc-F2:
                                          (SEQ ID NO: 12)
5'-GACTACAAGG ACGACGATGA CAAGGACAAA
ACTCACACAT GCCCACCGTG CCCAGCTCCG GAACTCC-3'

FlagFc-R2:
                                          (SEQ ID NO: 13)
5'-TAGTGGATCCTCATTTACCCG-3'.
```

The pcDNA 3.1-Fc template was then added to two separate PCR reactions containing 50 pmol each of the primer pairs FlagFc-F1/R1 or FlagFc-F2/R2 in a 50 µl reaction using Pfu Ultra DNA polymerase (Stratagene, Calif.) according to manufacturer's standard protocol in a MJ Thermocycler using the following cycles: 95° C. 2 minutes; 30 cycles of (95° C. 30 seconds, 52° C. 30 seconds, 72° C. 45 seconds), followed by 72° C. for 10 minutes. The products of these two reactions were then mixed in another PCR reaction (2 µl each) with 50 pmol of FlagFc-F1 and FlagFc-R2 primers in a 50 µl reaction using Pfu Ultra DNA polymerase (Stratagene, Calif.) according to manufacturer's standard protocol in a MJ Thermocycler using the following cycles: 95° C. 2 minutes; 30 cycles of (95° C. 30 seconds, 52° C. 30 seconds, 72° C. 45 seconds), followed by 72° C. for 10 minutes. The resulting fragment was gel purified, digested and inserted into the pcDNA 3.1-Fc plasmid NheI-BamHI. The resulting plasmid contains the mouse Igκ signal sequence producing the FlagFc protein.

Example 2

Cloning of PACE Construct

The coding sequence for human PACE (paired basic amino acid cleaving enzyme), an endoprotease, was obtained by RT-PCR. The following primers were used:

```
PACE-F1:
                                          (SEQ ID NO: 14)
5'-GGTAAGCTTGCCATGGAGCTGAGGCCCTGGTTGC-3'

PACE-R1:
                                          (SEQ ID NO: 15)
5'-GTTTTCAATCTCTAGGACCCACTCGCC-3'
```

-continued

PACE-F2:
(SEQ ID NO: 16)
5'-GCCAGGCCACATGACTACTCCGC-3'

PACE-R2:
(SEQ ID NO: 17)
5'-GGTGAATTCTCACTCAGGCAGGTGTGAGGGCAGC-3'.

The PACE-F1 primer adds a HindIII site to the 5' end of the PACE sequence beginning with 3 nucleotides before the start codon, while the PACE-R2 primer adds a stop codon after amino acid 715, which occurs at the end of the extracellular domain of PACE, as well as adding an EcoRI site to the 3' end of the stop codon. The PACE-R1 and -F2 primers anneal on the 3' and 5' sides of an internal BamHI site, respectively. Two RT-PCR reactions were then set up using 25 pmol each of the primer pairs of PACE-F1/R1 or PACE-F2/R2 with 20 ng of adult human liver RNA (Clontech; Palo Alto, Calif.) in a 50 µl RT-PCR reaction using the SuperScript.™ One-Step RT-PCR with PLATINUM® Taq system (Invitrogen, Carlsbad, Calif.) according to manufacturers protocol. The reaction was carried out in a MJ Thermocycler using the following cycles: 50° C. 30 minutes; 94° C. 2 minutes; 30 cycles of (94° C. 30 seconds, 58° C. 30 seconds, 72° C. 2 minutes), followed by 72° C. 10 minutes. These fragments were each ligated into the vector pGEM T-Easy (Promega, Madison, Wis.) and sequenced fully. The F2-R2 fragment was then subcloned into pcDNA6 V5/His (Invitrogen, Carlsbad, Calif.) using the BamHI/EcoRI sites, and then the F1-R1 fragment was cloned into this construct using the HindIII/BamHI sites. The final plasmid, pcDNA6-PACE, produces a soluble form of PACE (amino acids 1-715), as the transmembrane region has been deleted. The sequence of PACE in pcDNA6-PACE is essentially as described in Harrison et al. 1998, Seminars in Hematology 35:4.

Example 3

Cloning of Fc-Factor VII Construct

The coding sequence for Factor VII, was obtained by RT-PCR from human fetal liver RNA (Clontech, Palo Alto, Calif.). The Cloned region is comprised of the cDNA sequence from bp 36 to bp 1430 terminating just before the stop codon. A SbfI site was introduced on the N-terminus. A BspEI site was introduced on the C-terminus. The construct was cloned by PCR using the primers:

Downstream:
(SEQ ID NO: 18)
5' GCTACCTGCAGGCCACCATGGTCTCCCAGGCCCTCAGG 3'

Upstream:
(SEQ ID NO: 19)
5' CAGTTCCGGAGCTGGGCACGGCGGGCACGTGTGAGTTT
TGTCGGGAAAT GG 3' and the following conditions: 95° C. for 5 minutes followed by 30 cycles of 95° C. for 30 seconds. 55° C. for 30 seconds, 72° C. for 1 minute and 45 seconds, and a final extension cycle of 72° C. for 10 minutes.

The fragment was digested SbfI-BspEI and inserted into pED.dC-Fc a plasmid encoding for the Fc fragment of an IgG1.

Example 4

Factor VII-Fc Monomer-Dimer Hybrid Expression and Purification

CHO DG-44 cells expressing Factor VII-Fc were established. CHO DG-44 cells were grown at 37° C., 5% CO2, in MEM Alpha plus nucleoside and ribonucleosides and supplemented with 5% heat-inactivated fetal bovine serum until transfection.

DG44 cells were plated in 100 mm tissue culture petri dishes and grown to a confluency of 50%-60%. A total of 10 µg of DNA was used to transfect one 100 mm dish: either 9 µg pED.dC.FVII-Fc+1 µg of pcDNA6-PACE for the dimer transfection, or 7.5 µg of pED.dC.FVII-Fc+1.5 µg pcDNA3/Flag-Fc+1 µg of pcDNA6-PACE for the monomer transfection. The cells were transfected as described in the Superfect transfection reagent manual (Qiagen, Valencia, Calif.). The media was removed after 48 hours and replaced with MEM Alpha without nucleosides plus 5% dialyzed fetal bovine serum and 10 µg/ml of Blasticidin (Invitrogen, Carlsbad, Calif.) for both transfections, while the monomer-dimer hybrid transfection was also supplemented with 0.2 mg/ml geneticin (Invitrogen, Carlsbad, Calif.). After 10 days, the cells were released from the plate with 0.25% trypsin and transferred into T25 tissue culture flasks, and the selection was continued for 10-14 days until the cells began to grow well as stable cell lines were established. Protein expression was subsequently amplified by the addition 25 nM methotrexate.

Approximately $2 \times 10^7$ cells were used to inoculate 300 ml of growth medium in a 1700 $cm^2$ roller bottle (Corning, Corning, N.Y.) supplemented with 5 µg/L of vitamin $K_3$ (menadione sodium bisulfite) (Sigma, St Louis, Mo.). The roller bottles were incubated in a 5% $CO_2$ at 37° C. for 72 hours. The growth medium was then exchanged with 300 ml serum-free production medium (DMEM/F12 with 5 µg/ml bovine insulin and 10 µg/ml Gentamicin) supplemented with 5 µg/L of vitamin $K_3$. The production medium (conditioned medium) was collected every day for 10 days and stored at 4° C. Fresh production medium was added to the roller bottles after each collection and the bottles were returned to the incubator. Pooled media was first clarified using a Sartoclean glass fiber filter (3.0 µm+0.2 µm) (Sartorious Corp. Gottingen, Germany) followed by an Acropack 500 filter (0.8 µm+0.2 µm) (Pall Corp., East Hills, N.Y.). The clarified media was then concentrated approximately 20-fold using Pellicon Biomax tangential flow filtration cassettes (10 kDa MWCO) (Millipore Corp., Billerica, Mass.).

Figure 2:
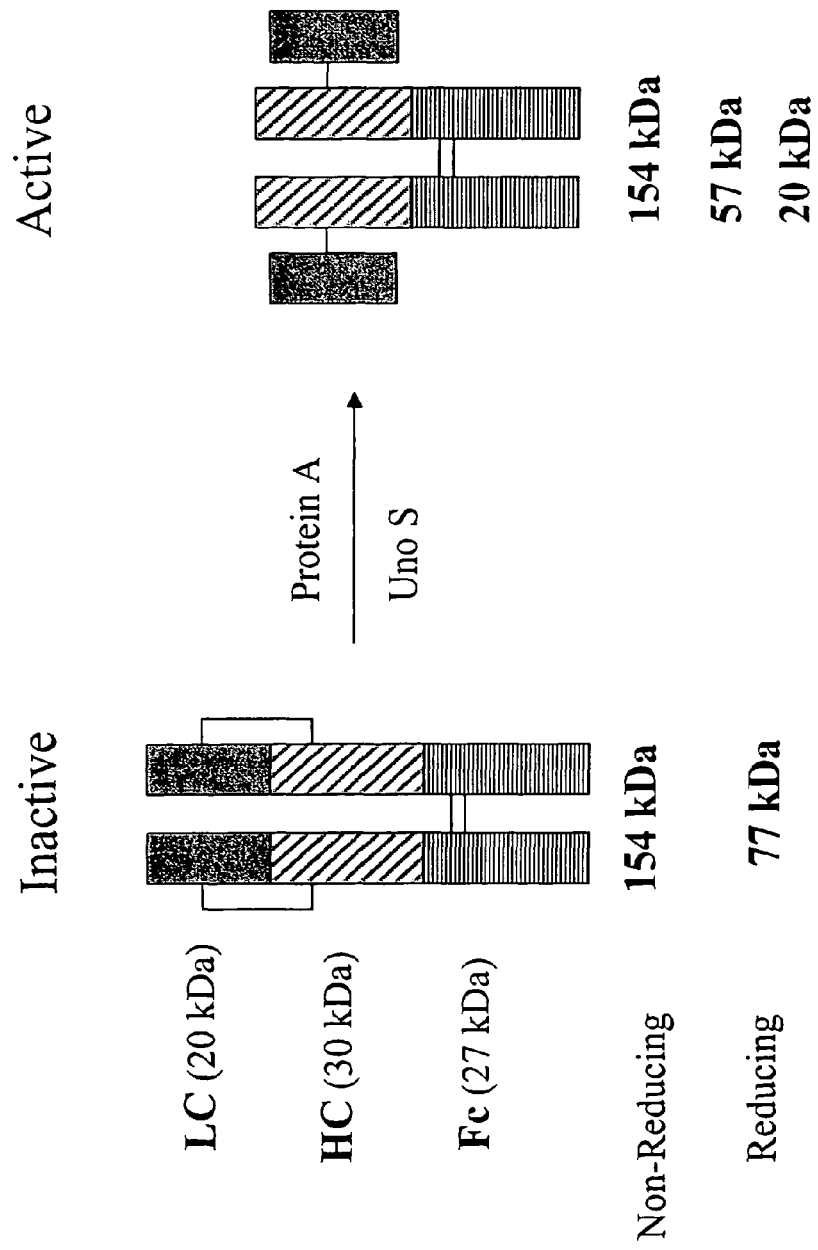
FIG. 2 is a diagram of the inactive and active forms of factor VIIa-Fc.

Fc chimeras were then captured from the concentrated media by passage over a Protein A Sepharose 4 Fast Flow Column (AP Biotech, Piscataway, N.J.). A 5×5 cm (100 ml) column was loaded with ≦5 mg Fc protein per ml column volume at a linear flow rate of 100 cm/hour to achieve a residence time of ≧3 minutes. The column was then washed with >5 column volumes of 1×DPBS to remove non-specifically bound proteins. The bound proteins were eluted with 100 mM Glycine pH 3.0. Elution fractions containing the protein peak were then neutralized by adding 1 part 1 M Tris-HCL, pH 8 to 10 parts elute fraction. Passage of the chimeric protein over the Protein A column converted inactive factor VII to activated factor VIIa (FIG. 2). Further activation could be achieved by passing the protein over an anion exchange column (Peders et al. 1989, *Biochemistry* 28:9331-36).

The monomer-dimer hybrid transfection protein sample was subject to further purification, as it contained a mixture of FVII-Fc:FVII-Fc homodimer, FVII-Fc: FLAG-Fc monomer-dimer hybrid, and FLAG-Fc: FLAG-Fc homodimers. To remove FLAG-Fc homodimers from the preparation, the Protein A Sepharose 4 Fast Flow pool was first dialyzed into 20 mM MES, 20 mM NaCl, pH 6.1 and was then passed over a Unosphere S cation-exchange column (BioRad Corp., Richmond, Calif.). Under the operating conditions for the column, the FLAG-Fc monomer-dimer hybrid has a net neutral charge (FLAG-Fc theoretical pI=6.19) and flows through the column while the hFVII-Fc constructs are positively charged, and thus bind to the column and elute at higher ionic strength. The dialyzed material was then loaded onto a 1.1×11 cm (9.9 ml) column at 150 cm/hour. During the wash and elution, the flow rate was increased to 500 cm/hour. The column was washed sequentially with 8 column volumes of 20 mM MES, 20 mM NaCl, pH 6.1 and 8 column volumes of 20 mM MES, 40 mM NaCl, pH 6.1. The bound protein was eluted with 20 mM MES, 750 mM NaCl, pH 6.1. Elution fractions containing the protein peak were pooled and sterile filtered through a 0.2 μm filter disc prior to storage at −80° C.

An anti-FLAG MAB affinity column was used to separate chimeric Fc dimers with hFVII fused to both Fc molecules from those with one FLAG peptide and one hFVII fusion. The Unosphere S Eluate pool was diluted 1:1 with 20 mM Tris, 50 mM NaCl, 5 mM $CaCl_2$, pH 8 and loaded onto a 1.6×5 cm M2 anti-FLAG sepharose column (Sigma Corp., St. Louis, Mo.) at a linear flow rate of 60 cm/hour. Loading was targeted to <2.5 mg monomer-dimer hybrid/ml column volume. After loading the column was washed with 5 column volumes 20 mM Tris, 50 mM NaCl, 5 mM $CaCl_2$, pH 8.0. monomer-dimer hybrids were then eluted with 100 mM Glycine, pH 3.0. Elution fractions containing the protein peak were then neutralized by adding 1 part 1 M Tris-HCl, pH 8 to 10 parts eluate fraction. Pools were stored at −80° C.

Example 5

Clotting Activity Analysis of Factor VII-Fc Homodimer and Monomer/Dimer Hybrids

Figure 4:
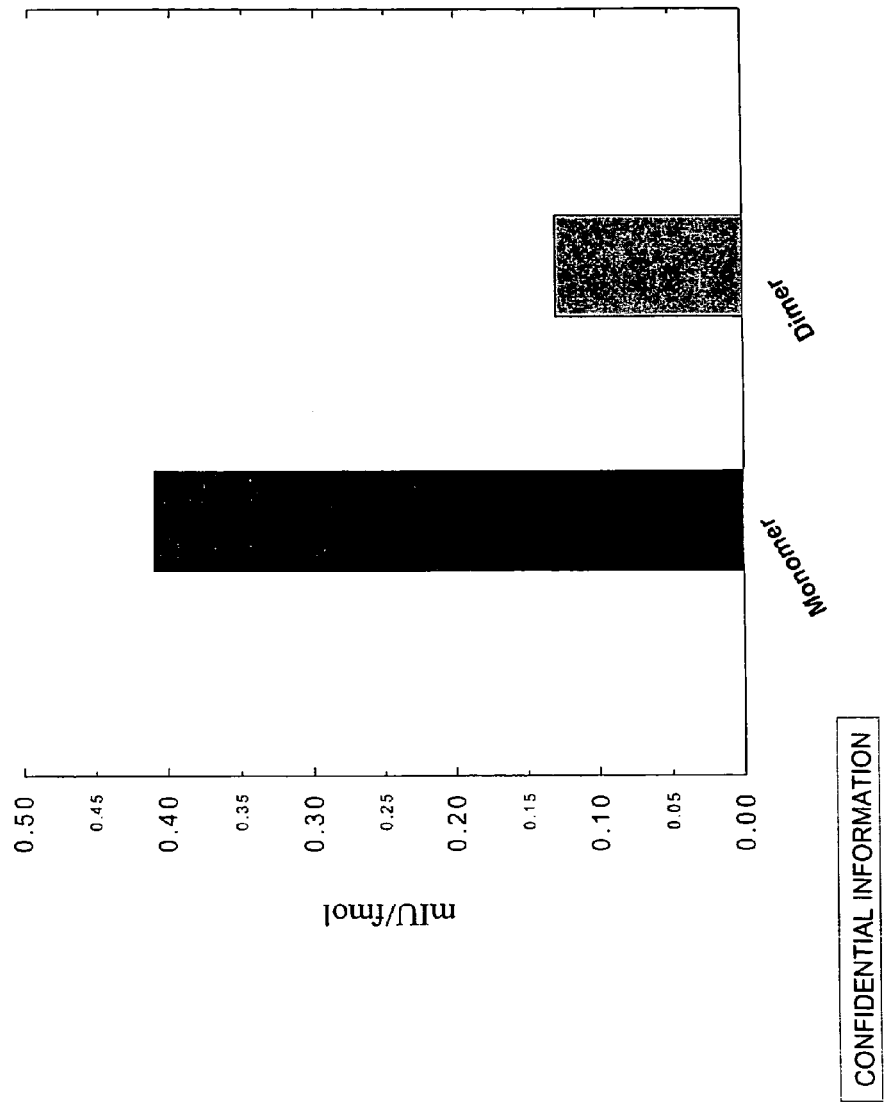
FIG. 4 is a diagram of results from a STA-CLOT assay showing factor VIIa-Fc has significant clotting activity.

The StaClot FVIIa-rTF assay kit was purchased from Diagnostica Stago (Parsippany, N.J.) and modified as described in Johannessen et al. 2000, *Blood Coagulation and Fibrinolysis* 11: S159. A standard curve was performed with the FVIIa World Health Organization standard 89/688. The assay compared a homodimer comprised of two factor VII molecules and two Fc molecules with a monomer/dimer hybrid comprised of one factor VII molecule and two Fc molecules. Significant clotting activity was observed for both the monomer/dimer hybrid and the homodimer. The clotting activity of the monomer/dimer hybrid compared to the homodimer was almost four times as great (FIG. 4).

Example 6

Binding of Factor VII-Fc to shFcRn

Figure 5:
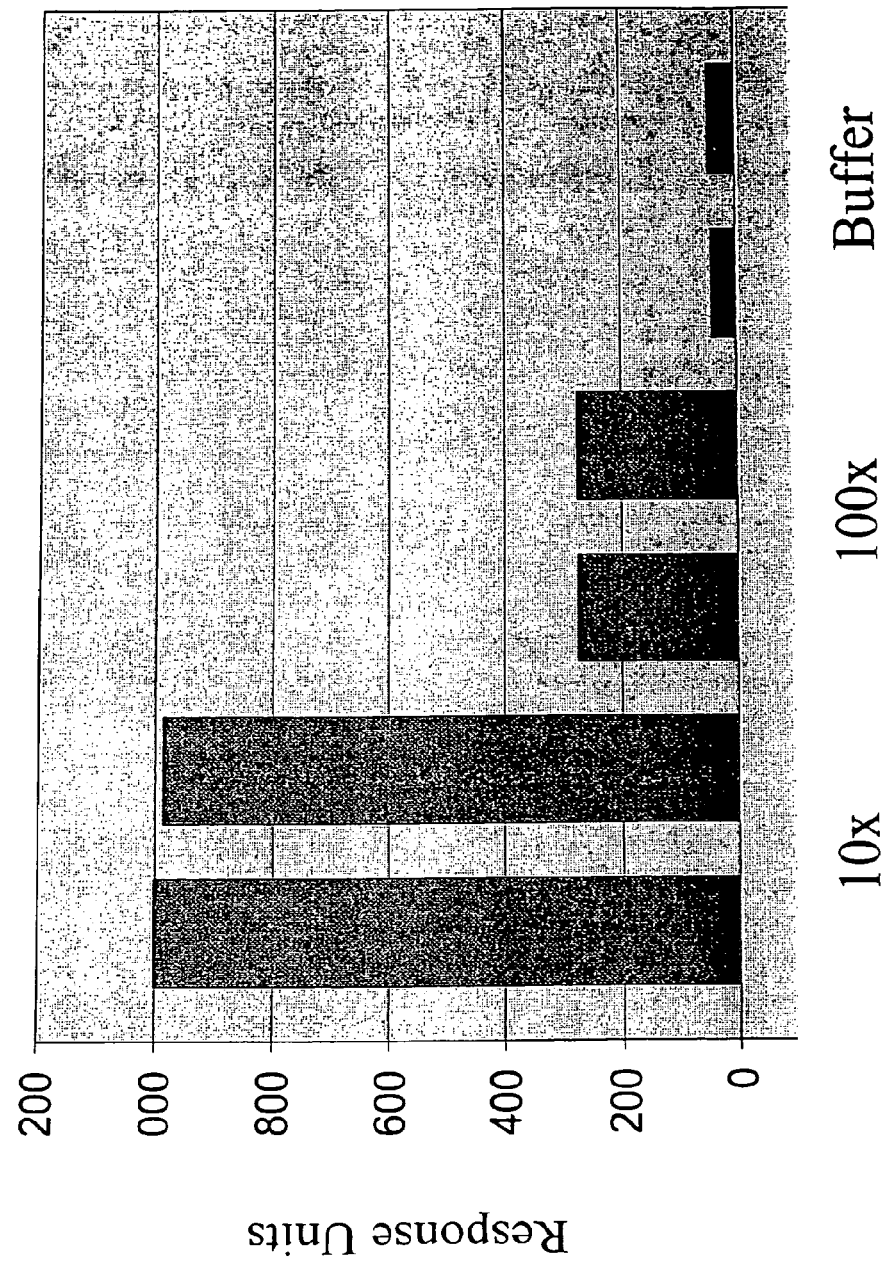
FIG. 5 is a diagram showing factor VIIa-Fc binds to soluble human Fc neonatal receptor (shFcRn).

Binding of factor VII-Fc to soluble human neonatal Fc receptor (shFcRn) was analyzed using a Biacore 3000 instrument (Biacore, Uppsala, Sweden). A CM5 chip (Biacore, Uppsala, Sweden) was coated with 3500 resonance units (RU) of shFcRn using amine chemistry. Factor VII-Fc was diluted, 10 fold or 100 fold, in 50 mM $PO_4$, pH 6.0, 100 mM NaCl, 0.01% Tween-20 and injected (in duplicate) over the surface for 10 minutes at 10 μL/minute. The samples were also injected over a mock-coated surface which served as a reference control. The chip was regenerated with 100 mM $PO_4$ pH 8.0. The response (in RU), recorded 30 seconds before the injection was stopped, indicated specific binding (FIG. 5).

Example 7

Factor VII-Fc Oral Uptake in Neonatal Rats 25 gram day 9 newborn rats were purchased from Charles River (Wilmington, Mass.) and allowed to acclimate for 24 hours. The rats were dosed orally with FVIIa-Fc homodimer, or monomer/dimer hybrid (consisting of two Fc chains, one of which was linked to Fc-VII). A volume of 200 μl of a FVIIa-Fc solution was used for a dose of 1 mg/kg. The solution was comprised of a Tris-HCl buffer pH 7.4 with 5 mg/ml soybean trypsin inhibitor. The rats were euthanized with $CO_2$ at several time points, and 200 μl of blood was drawn by cardiac puncture. Plasma was obtained by the addition of a ⅒ volume 3.8% sodium citrate solution and centrifuged at room temperature at a speed of 1268×g. The plasma samples were either used in the assays fresh or frozen at −20° C.

Figure 6:
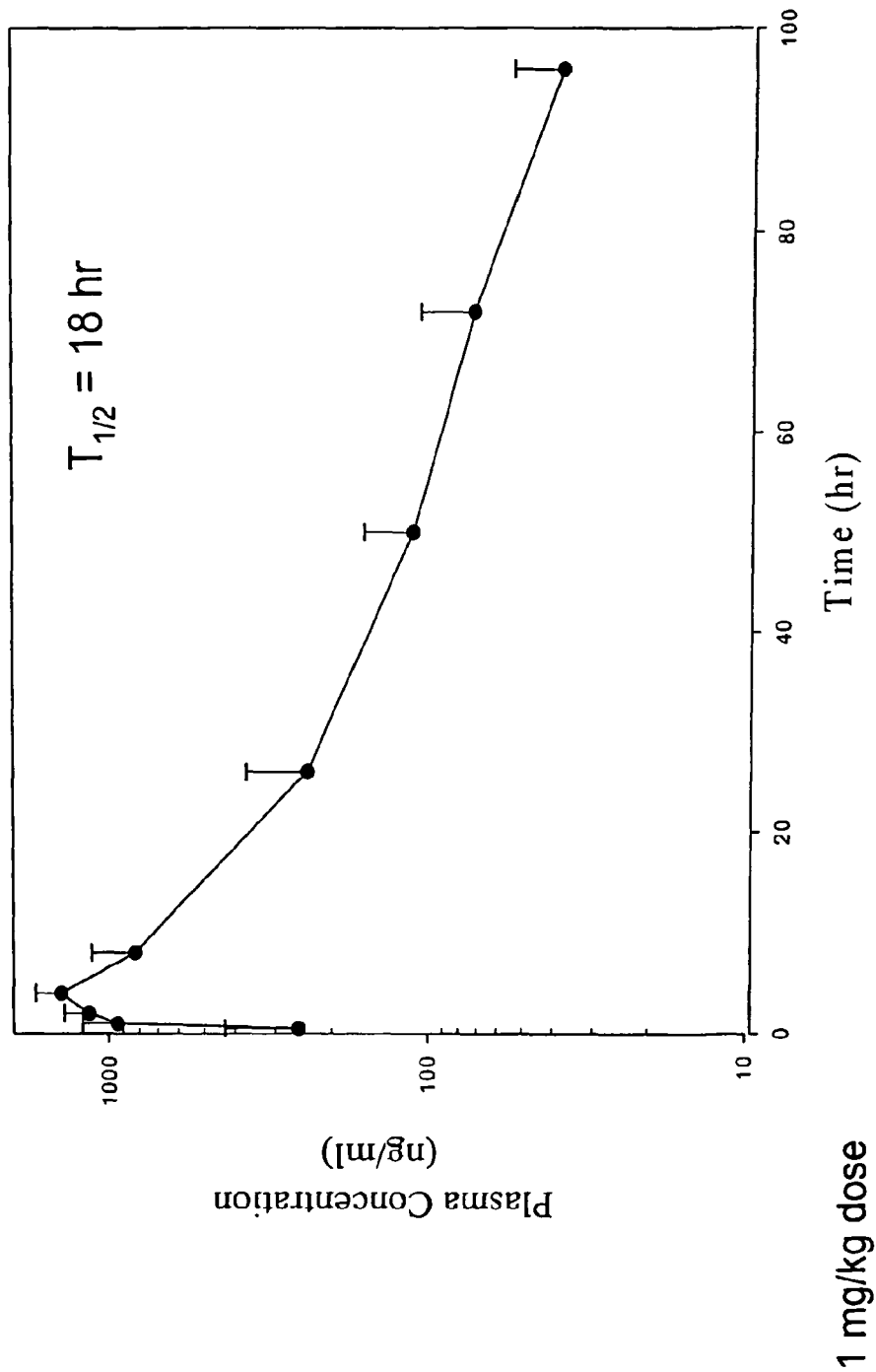
FIG. 6 demonstrates plasma levels over time for orally administered factor VIIa-Fc in neonatal rats.
Figure 7:
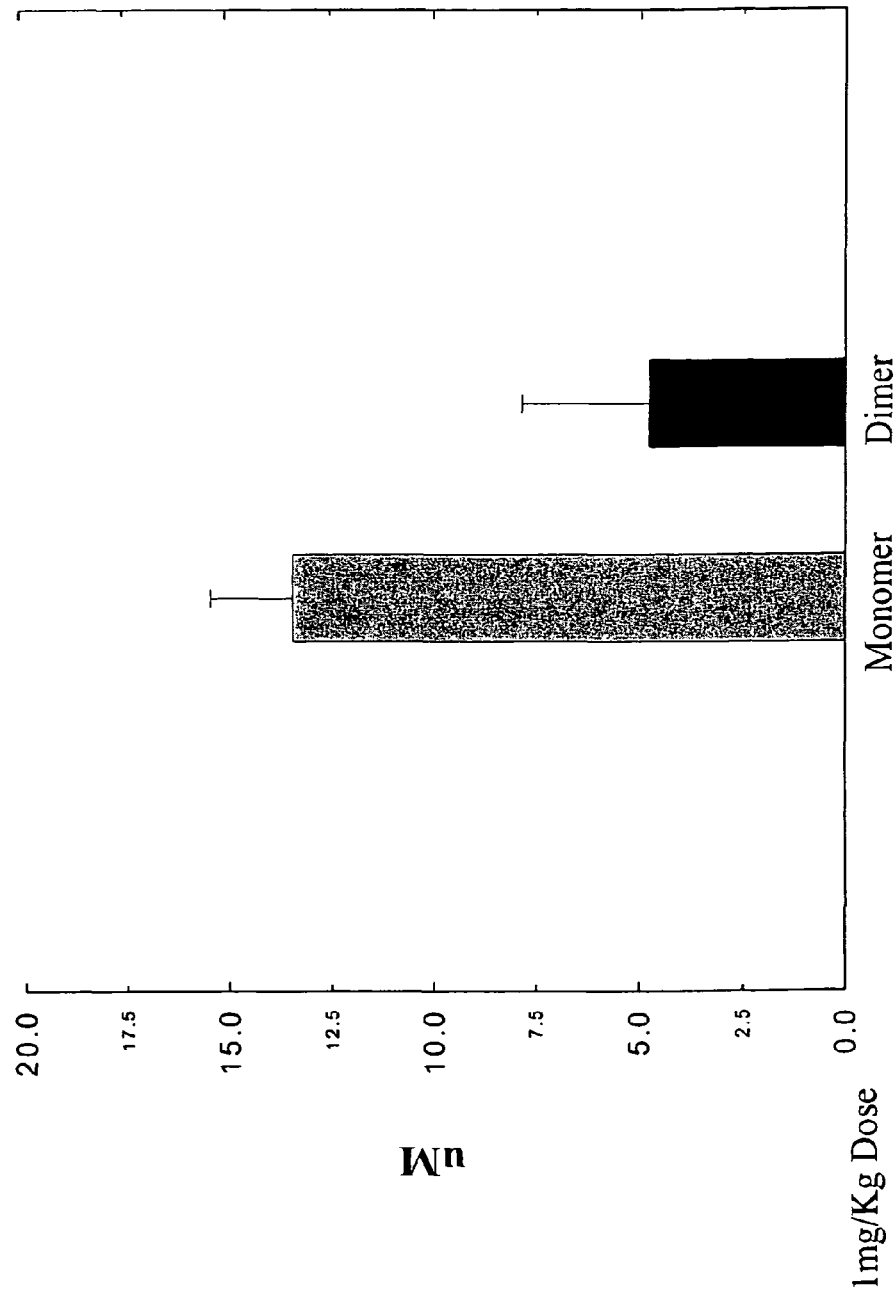
FIG. 7 compares oral uptake in neonatal rats of Factor VIIa-Fc monomer/dimer hybrids comprising two polypeptide chains, each chain comprising at least a portion of an immunoglobulin constant region and wherein factor VII is linked to only one of the two chains versus homodimers comprising two polypeptide chains wherein both chains comprise at least a portion of an immunoglobulin constant region and both chains also comprise factor VII.

Samples were then analyzed by ELISA. The Asserachrom Factor VII:Ag ELISA was performed on the neonatal rat plasma samples. A Factor VII:Ag ELISA assay was purchased from Diagnostica Stago (Parsippany, N.J.) and performed as described in the kit manual with one change. The standard for the standard curve was replaced with purified Factor VIIa-Fc. For in vivo experiments, the standard was run in the same percent normal animal plasma as being analyzed. The results showed oral administration of both the monomer/dimer hybrids and the dimers was successful (FIG. 7). A time course assay using monomer/dimer hybrids demonstrated sustained plasma levels of orally administered Factor VIIa-Fc over time with a $T_{1/2}$ of 18 hours (FIG. 6).

Example 8

Intravenous Dosing of Factor VII-Fc in Minipigs

Adult Gottingen minipigs (6 kg) were purchased from Marshall Farms and allowed to acclimate for two weeks. The pigs were anethestized with 12 mg/kg Telazol and 8 mg/kg Xylaxine and dosed intravenously through the jugular vein with 3 ml of a 0.5 mg/kg Factor VIIa-Fc solution in a Tris-HCl buffer pH 7.4. Three mls of blood was collected in citrated vacutainer tubes (BD Sciences, Franklin Lakes, N.J.) at various time points via venous puncture. Plasma was obtained by centrifuging samples at room temperature at a speed of 1268× g. The plasma samples were frozen at −20° C. and subsequently analyzed by ELISA.

Figure 8A:
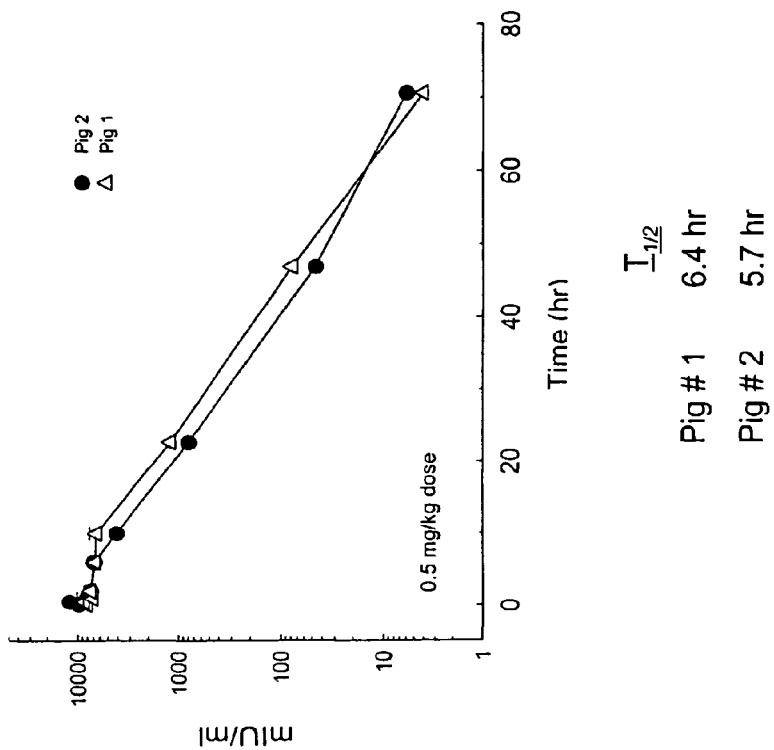
FIG. 8A demonstrates plasma levels over time of factor VIIa-Fc administered intravenously to minipigs, wherein the factor VIIa-Fc is a monomer/dimer hybrid comprising two polypeptide chains, each chain comprising at least a portion of an immunoglobulin constant region and wherein factor VII is linked to only one of the two chains.

The Asserachrom Factor VII:Ag ELISA was performed on the minipig samples. A Factor VII:Ag Elisa assay was purchased from Diagnostica Stago (Parsippany, N.J.) and preformed as described in the kit manual with one change. The standard for the standard curve was replaced with purified Factor VIIa-Fc. For in vivo experiments, the standard was run in the same percent normal animal plasma as being analyzed. Plasma levels of intravenously administered monomer/dimer hybrid are shown in FIG. 8A. The half life was determined to be 9.4 hours. A time course assay using monomer/dimer hybrid chimeric protein demonstrated sustained plasma levels of intravenously administered Factor VIIa-Fc over time with a $T_{1/2}$ of 22 hours (FIG. 8A).

Figure 8B:
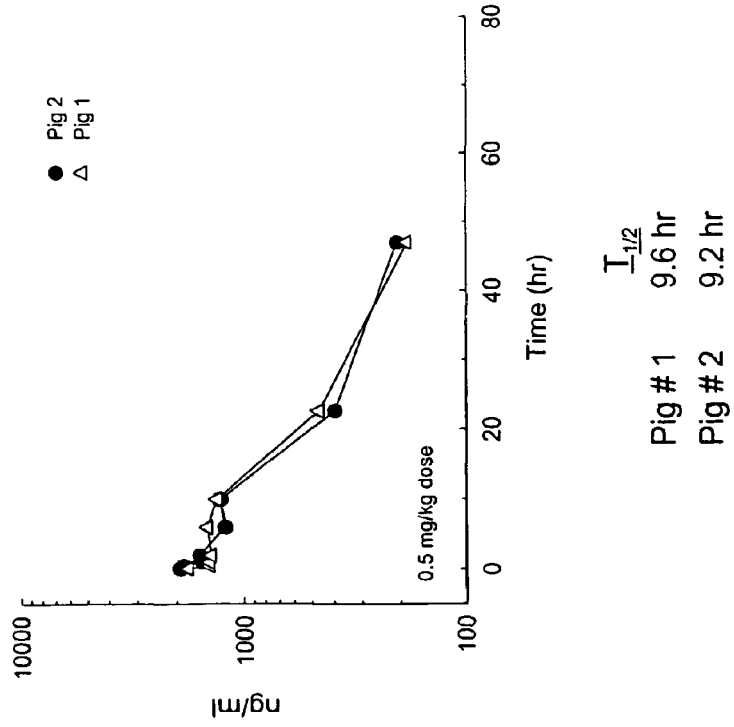
FIG. 8B demonstrates clotting activity over time of factor VIIa-Fc administered intravenously to minipigs wherein the factor VIIa-Fc is a monomer/dimer hybrid comprising two polypeptide chains, each chain comprising at least a portion of an immunoglobulin constant region and wherein factor VII is linked to only one of the two chains.

Clotting activity using was measured by the StaClot FVIIa-rTF assay kit (FIG. 8B). The $T_{1/2}$ for clotting was found to be 6.4 hours for one pig and 5.7 for the other pig.

Example 9

Cloning of Fc-Factor IX construct

The human Factor IX coding sequence, including the pre-propeptide sequence, was obtained by RT-PCR amplification from adult human liver RNA using the following primers:

```
natFIX-F:
                                       (SEQ ID NO: 20)
5'-TTACTGCAGAAGGTTATGCAGCGCGTGAACATG-3'

F9-R:
                                       (SEQ ID NO: 21)
5'-TTTTTCGAATTCAGTGAGCTTTGTTTTTCCTTAATCC-3'
```

20 ng of adult human liver RNA (Clontech, Palo Alto, Calif.) and 25 pmol each primer were added to a RT-PCR reaction using the SuperScript.™ One-Step RT-PCR with PLATINUM® Taq system (Invitrogen, Carlsbad, Calif.) according to manufacturers protocol. Reaction was carried out in a MJ Thermocycler using the following cycles: 50° C. 30 minutes; 94° C. 2 minutes; 35 cycles of (94° C. 30 seconds, 58° C. 30 seconds, 72° C. 1 minute), and a final 72° C. 10 minutes. The fragment was gel purified using Qiagen Gel Extraction Kit (Qiagen, Valencia, Calif.), and digested with PstI-EcoRI, gel purified, and cloned into the corresponding digest of the pED.dC.XFc plasmid. The amino acid and DNA sequences of factor IX-Fc are shown in FIG. 9.

Example 10

Factor IX-Fc Homodimer and Monomer-Dimer Hybrid Expression and Purification

CHO DG-44 cells expressing Factor IX-Fc were established. DG44 cells were plated in 100 mm tissue culture petri dishes and grown to a confluency of 50%-60%. A total of 10 μg of DNA was used to transfect one 100 mm dish: for the homodimer transfection, 8 μg of pED.dC.Factor IX-Fc+2 μg of pcDNA6-PACE was used; for the monomer-dimer hybrid transfection, 8 μg of pED.dC.Factor IX-Fc+1 μg of pcDNA3-FlagFc+1 μg pcDNA6-PACE was used. The cells were transfected as described in the Superfect transfection reagent manual (Qiagen, Valencia, Calif.). The media was removed from transfection after 48 hours and replaced with MEM Alpha without nucleosides plus 5% dialyzed fetal bovine serum and 10 μg/ml of Blasticidin (Invitrogen, Carlsbad, Calif.) for both transfections, while the monomer-dimer hybrid transfection was also supplemented with 0.2 mg/ml geneticin (Invitrogen, Carlsbad, Calif.). After 3 days, the cells were released from the plate with 0.25% trypsin and transferred into T25 tissue culture flasks, and the selection was continued for 10-14 days until the cells began to grow well as stable cell lines were established. Protein expression was subsequently amplified by the addition 10 nM or 100 nM methotrexate for the homodimer or monomer-dimer hybrid, respectively.

For both cell lines, approximately $2 \times 10^7$ cells were used to inoculate 300 ml of growth medium in a 1700 $cm^2$ roller bottle (Corning, Corning, N.Y.), supplemented with 5 μg/L of vitamin $K_3$ (menadione sodium bisulfite) (Sigma, St. Louis, Mo.). The roller bottles were incubated in a 5% $CO_2$ at 37° C. for approximately 72 hours. The growth medium was exchanged with 300 ml serum-free production medium (DMEM/F12 with 5 μg/ml bovine insulin and 10 μg/ml Gentamicin), supplemented with 5 μg/L of vitamin $K_3$. The production medium (conditioned medium) was collected everyday for 10 days and stored at 4° C. Fresh production medium was added to the roller bottles after each collection and the bottles were returned to the incubator. Prior to chromatography, the medium was clarified using a SuporCap-100 (0.8/0.2 μm) filter from Pall Gelman Sciences (Ann Arbor, Mich.). All of the following steps were performed at 4° C. The clarified medium was applied to Protein A Sepharose, washed with 5 column volumes of 1×PBS (10 mM phosphate, pH 7.4, 2.7 mM KCl, and 137 mM NaCl), eluted with 0.1 M glycine, pH 2.7, and then neutralized with ¹⁄₁₀ volume of 1 M Tris-HCl, pH 9.0. The protein was then dialyzed into PBS.

The monomer-dimer hybrid transfection protein sample was subject to further purification, as it contained a mixture of FIX-Fc:FIX-Fc homodimer, FIX-Fc:Flag-Fc monomer-dimer hybrid, and Flag-Fc:Flag-Fc homodimer. Material was concentrated and applied to a 2.6 cm×60 cm (318 ml) Superdex 200 Prep Grade column at a flow rate of 4 ml/minute (36 cm/hour) and then eluted with 3 column volumes of 1×PBS. Fractions corresponding to two peaks on the UV detector were collected and analyzed by SDS-PAGE. Fractions from the first peak contained either FIX-Fc:FIX-Fc homodimer or FIX-Fc:FlagFc monomer-dimer hybrid, while the second peak contained FlagFc:FlagFc homodimer. All fractions containing the monomer-dimer hybrid but no FlagFc homodimer were pooled and applied directly to a 1.6×5 cm M2 anti-FLAG sepharose column (Sigma Corp., St. Louis, Mo.) at a linear flow rate of 60 cm/hour. After loading, the column was washed with 5 column volumes PBS. Monomer-dimer hybrids were then eluted with 100 mM Glycine, pH 3.0. Elution fractions containing the protein peak were then neutralized by adding ¹⁄₁₀ volume of 1 M Tris-HCl, and analyzed by reducing and nonreducing SDS-PAGE. Fractions were dialyzed into PBS, concentrated to 1-5 mg/ml, and stored at −80° C.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. A chimeric protein comprising a first polypeptide chain and a second polypeptide chain,
wherein said first chain comprises (i) a clotting factor, which is Factor VII or Factor VIIa, and (ii) an immunoglobulin constant region or portion thereof fused to the clotting factor, which is a neonatal Fc Receptor (FcRn) binding partner, and
said second chain comprises an immunoglobulin constant region or portion thereof, which is a FcRn binding partner, without the clotting factor of said first chain and without an immunoglobulin variable domain, and
wherein said first chain and said second chain are linked.

2. The chimeric protein of claim 1, wherein said clotting factor is fused to the immunoglobulin constant region or portion thereof by a linker.

3. The chimeric protein of claim 2, wherein the linker comprises about 1 to about 20 amino acids.

4. The chimeric protein of claim 2, wherein the linker comprises the sequence (GlyGlySer)n or SEQ ID NO: 31, wherein n is an integer selected from the group consisting of 1, 2, 3, 4, 5, 6, 7, 8, 9, and 10.

5. The chimeric protein of claim 1, wherein the portion of an immunoglobulin constant region of the first chain is an Fc fragment.

6. The chimeric protein of claim 5, wherein the portion of an immunoglobulin constant region of the second chain is an Fc fragment.

7. The chimeric protein of claim 5, wherein the Fc fragment comprises an amino acid sequence having at least 80% identity with the sequence set forth in SEQ ID NO: 3, wherein said amino acid sequence binds to FcRn.

8. The chimeric protein of claim 6, wherein the Fc fragment comprises an amino acid sequence having at least 80% identity with the sequence set forth in SEQ ID NO: 3, wherein said amino acid sequence hinds to FcRn.

9. The chimeric protein of claim 1, wherein the immunoglobulin constant region or portion thereof of the first chain and the immunoglobulin constant region or portion thereof of the second chain are identical.

10. The chimeric protein of claim 1, wherein said first chain and said second chain are linked covalently or non-covalently.

11. The chimeric protein of claim 1, Wherein said first chain and second chain are linked via a disulfide bond.

12. The chimeric protein of claim 1, wherein said second chain consists of the immunoglobulin constant region or portion thereof comprising a FcRn biding partner.

13. A pharmaceutical composition comprising the chimeric protein of claim 1 and a pharmaceutically acceptable carrier.

14. The composition of claim 13, which promotes hemostasis.

15. The composition of claim 14, which is formulated for oral administration, buccal administration, sublingual administration, intravenous injection, subcutaneous injection, intramuscular injection, nasal administration, rectal administration, vaginal administration, pulmonary administration, or inhalation.

16. The composition of claim 13, further comprising at least one agent, which is capable of treating a disease or condition.

17. The composition of claim 16, Wherein said at least one agent is a protein comprising a clotting factor.

18. The composition of claim 17, wherein said clotting factor is selected from the group consisting of Factor V, Factor VII, Factor VIIa, Factor VIII, Factor VIIIa, Factor IX, Factor IXa, Factor X, Factor Xa, Factor XI, Factor XII, Factor XIII, fibrinogen, prothrombin, von Willebrand factor, and a combination thereof.

19. A chimeric protein having the formula:

X-L-F:F or F:F-L-X wherein F is an immunoglobulin constant region or portion thereof comprising an FcRn binding partner, L is a linker or a direct bond, X is Factor VII or Factor VIIa, and: is a covalent or non-covalent bond.

20. The chimeric protein of claim 19, wherein said F is an Fc fragment.

21. The chimeric protein of claim 19, wherein said F in X-L-F and said F in F are identical.

22. The chimeric protein of claim 19, wherein the linker comprises about 1 to about 20 amino acids.

23. The chimeric protein of claim 22, wherein the linker comprises the sequence (GlyGlySer)n or SEQ ID NO: 31, wherein n is an integer selected from the group consisting of 1, 2, 3, 4, 5, 6, 7, 8, 9, and 10.

24. The chimeric protein of claim 19, wherein said (:) is a disulfide bond.

* * * * *

SEQUENCE LISTING

<160> NUMBER OF SEQ ID NOS: 32

<210> SEQ ID NO 1
<211> LENGTH: 664
<212> TYPE: PRT
<213> ORGANISM: Artificial Sequence
<220> FEATURE:
<223> OTHER INFORMATION: Description of Artificial Sequence: Synthetic amino acid construct

<400> SEQUENCE: 1

```
Ala Asn Ala Phe Leu Leu Glu Glu Leu Arg Pro Gly Ser Leu Glu Arg
1               5                   10                  15

Glu Cys Lys Glu Glu Gln Cys Ser Phe Glu Glu Ala Arg Glu Ile
            20                  25                  30

Phe Lys Asp Ala Glu Arg Thr Lys Leu Phe Trp Ile Ser Tyr Ser Ser
            35                  40                  45

Asp Gly Asp Gln Cys Ala Ser Ser Pro Cys Gln Asn Gly Gly Ser Cys
        50                  55                  60

Lys Asp Gln Leu Leu Gln Ser Tyr Ile Cys Phe Cys Leu Pro Ala Phe
65                  70                  75                  80

Glu Gly Arg Asn Cys Glu Thr His Lys Lys Asp Asp Gln Leu Ile Cys
                85                  90                  95

Val Asn Glu Asn Gly Gly Cys Glu Gln Tyr Cys Ser Asp His Thr
            100                 105                 110

Gly Thr Lys Arg Ser Cys Arg Cys His Glu Gly Tyr Ser Leu Leu Ala
            115                 120                 125

Asp Gly Val Ser Cys Thr Pro Thr Val Glu Tyr Pro Cys Gly Lys
        130                 135                 140

Ile Pro Ile Leu Glu Lys Arg Asn Asn Ala Ser Lys Pro Gln Gly Arg
145                 150                 155                 160

Ile Val Gly Gly Lys Val Cys Pro Lys Gly Glu Cys Pro Trp Gln
                165                 170                 175

Val Leu Leu Leu Val Asn Gly Ala Gln Leu Cys Gly Gly Thr Leu Ile
            180                 185                 190

Asn Thr Thr Ile Trp Val Val Ser Ala Ala His Cys Phe Asp Lys Ile
            195                 200                 205

Lys Asn Trp Arg Asn Leu Ile Ile Ala Val Leu Gly Glu His Asp Leu
        210                 215                 220

Ser Glu His Asp Gly Asp Glu Gln Ser Arg Arg Val Val Ala Gln Val
225                 230                 235                 240

Ile Ile Pro Ser Thr Tyr Val Pro Gly Thr Thr Asn His Asp Ile Ala
                245                 250                 255

Leu Leu Leu Arg Leu His Gln Pro Val Val Leu Thr Asp His Val Val
            260                 265                 270

Pro Leu Cys Leu Pro Glu Arg Thr Phe Ser Glu Arg Thr Leu Ala
            275                 280                 285

Phe Val Arg Phe Ser Leu Val Ser Gly Trp Gly Gln Leu Leu Asp
        290                 295                 300

Arg Gly Ala Thr Ala Leu Glu Leu Met Val Leu Asn Val Pro Arg Leu
305                 310                 315                 320

Leu Met Thr Gln Asp Cys Leu Gln Gln Ser Arg Lys Val Gly Asp Ser
                325                 330                 335

Pro Asn Ile Thr Glu Glu Tyr Met Phe Cys Ala Gly Tyr Ser Asp Gly
            340                 345                 350
```

```
Ser Lys Asp Ser Cys Lys Gly Asp Ser Gly Gly Pro His Ala Thr
        355                 360                 365

His Tyr Arg Gly Thr Trp Tyr Leu Thr Gly Ile Val Ser Trp Gly
    370                 375                 380

Gln Gly Cys Ala Thr Val Gly His Phe Gly Val Tyr Thr Arg Val Ser
385                 390                 395                 400

Gln Tyr Ile Glu Glu Trp Leu Gln Lys Leu Met Arg Ser Glu Pro Arg
                405                 410                 415

Pro Gly Val Leu Leu Arg Ala Pro Phe Phe Pro Asp Lys Thr His Thr
                420                 425                 430

Cys Pro Pro Cys Pro Ala Pro Glu Leu Leu Gly Gly Pro Ser Ser Val
            435                 440                 445

Phe Leu Phe Pro Pro Lys Pro Lys Asp Thr Leu Met Ile Ser Arg Thr
        450                 455                 460

Pro Glu Val Val Thr Cys Val Val Val Asp Val Ser His Glu Asp Pro
465                 470                 475                 480

Glu Val Lys Phe Asn Trp Tyr Val Asp Gly Val Glu Val His Asn
                485                 490                 495

Ala Lys Thr Lys Pro Arg Glu Glu Gln Tyr Asn Ser Thr Tyr Arg
                500                 505                 510

Val Val Ser Val Leu Thr Val Leu His Gln Asp Trp Leu Asn Gly Lys
            515                 520                 525

Glu Tyr Tyr Lys Cys Lys Val Ser Asn Lys Ala Leu Pro Ala Pro Ile
        530                 535                 540

Glu Lys Thr Ile Ser Lys Ala Ala Lys Gly Gln Pro Arg Glu Pro Gln
545                 550                 555                 560

Val Tyr Thr Leu Pro Pro Ser Arg Asp Glu Leu Thr Lys Asn Gln
                565                 570                 575

Val Ser Leu Thr Cys Leu Val Lys Gly Phe Tyr Pro Ser Asp Ile Ala
            580                 585                 590

Val Val Glu Trp Glu Ser Asn Gly Gln Pro Glu Asn Asn Tyr Lys Thr
        595                 600                 605

Thr Pro Val Leu Asp Asp Ser Asp Gly Ser Phe Phe Leu Tyr Ser Lys
        610                 615                 620

Leu Thr Val Asp Lys Ser Arg Trp Gln Gln Gly Asn Val Phe Ser
625                 630                 635                 640

Cys Ser Val Met His Glu Ala Leu His Asn His Tyr Thr Gln Lys Lys
                645                 650                 655

Ser Leu Ser Leu Ser Pro Gly Lys
                660

<210> SEQ ID NO 2
<211> LENGTH: 239
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 2

Phe Pro Asp Lys Thr His Thr Cys Pro Pro Cys Pro Ala Pro Glu Leu
1               5                   10                  15

Leu Gly Gly Pro Ser Ser Val Phe Leu Phe Pro Pro Lys Pro Lys Asp
            20                  25                  30

Thr Leu Met Ile Ser Arg Thr Pro Glu Val Val Thr Cys Val Val Val
        35                  40                  45
```

Asp Val Ser His Glu Asp Pro Glu Val Lys Phe Asn Trp Tyr Val Val
50                  55                  60

Asp Gly Val Glu Val His Asn Ala Lys Thr Lys Pro Arg Glu Glu Gln
65                  70                  75                  80

Tyr Asn Ser Thr Thr Tyr Arg Val Val Ser Val Leu Thr Val Leu His
                85                  90                  95

Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Ala Lys
            115                 120                 125

Gly Gln Pro Arg Glu Pro Gln Val Tyr Thr Leu Pro Pro Ser Arg Asp
            130                 135                 140

Glu Leu Thr Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln
                165                 170                 175

Pro Glu Asn Asn Tyr Lys Thr Thr Pro Val Leu Asp Ser Asp Gly
            180                 185                 190

Ser Phe Phe Leu Tyr Ser Lys Leu Thr Val Asp Lys Ser Arg Trp Gln
                195                 200                 205

Gln Gln Gly Asn Val Phe Ser Cys Ser Val Met His Glu Ala Leu His
210                 215                 220

Asn His Tyr Thr Gln Lys Ser Leu Ser Leu Ser Pro Gly Lys
225                 230                 235

<210> SEQ ID NO 3
<211> LENGTH: 682
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3
gacaaaactc acacgtgccc gccgtgccca gctccggaac tgctgggcgg accgtcagtc      60
ttcctcttcc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaat     300
gtcaaggtct ccaacaaagc ccctcccagc cccatcgag aaaaccatct ccaaagccaa      360
agggcagccc cgagaaccac aggtgtacac cctgcccca tcccgggatg agctgaccaa      420
gaaccaggtc agcctgacct gcctggtcaa aggcttctat cccagcgaca tcgccgtgga     480
gtgggagagc aatgggcagc cggagaacaa ctacaagacc acgcctcccg tgttggactc     540
cgacggctcc ttcttcctct acagcaagct caccgtggac aagagcaggt ggcagcaggg     600
gaacgtcttc tcatgctccg tgatgcatga ggctctgcac aaccactaca cgcagaagag     660
cctctccctg tctccgggta aa                                              682

<210> SEQ ID NO 4
<211> LENGTH: 1900
<212> TYPE: DNA
<213> ORGANISM: Artificial Sequence
<220> FEATURE:
<223> OTHER INFORMATION: Description of Artificial Sequence: Synthetic
      nucleotide -continued construct

<400> SEQUENCE: 4

```
gccaacgcgt tcctggagga gctgcggccg ggctccctgg agagggagtg caaggaggag      60
cagtgctcct cgaggaggc ccgggagatc ttcaaggacg cggagaggac gaagctgttc     120
tggatttctt acagtgatgg ggaccagtgt gcctcaagtc catgccagaa tgggggctcc     180
tgcaaggacc agctccagtc ctatatctgc ttctgcctcc ctgccttcga gggccggaac     240
tgtgagacgc acaaggatga ccagctgatc tgtgtgaacg agaacggcgg ctgtgagcag     300
tactgcagtg accacacggg caccaagcgc tcctgtcggt gccacgaggg gtactctctg     360
ctggcagacg gggtgtcctg cacacccaca gttgaatatc catgtggaaa aatacctatt     420
ctagaaaaaa gaaatgccag caaacccaa ggccgaattg tgggggggcaa ggtgtgcccc     480
aaagggagt gtccatggca ggtcctgttg ttggtgaatg gagctcagtt gtgtgggggg     540
accctgatca acaccatctg gtggtctcc gcggcccact gtttcgacaa aatcaagaac     600
tggaggaacc tgatcgcggt gctgggcgag cacgacctca gcgagcacga cggggatgag     660
cagagccggc gggtggcgca ggtcatcatc cccagcacgt acgtcccggg caccaccaac     720
cacgacatcg cgctgctccg cctgcaccag cccgtggtcc tcactgacca tgtggtgccc     780
ctctgcctgc ccgaacggac gttctctgag aggacgctgg ccttcgtgcg cttctcattg     840
gtcagcggct ggggccagct gctggaccgt ggcgccacgg ccctggagct catggtcctc     900
aacgtgcccc ggctgatgac ccaggactgc ctgcagcagt cacggaaggt gggagactcc     960
ccaaatatca cggagtacat gttctgtgcc ggctactcgg atggcagcaa ggactcctgc    1020
aaggggggaca gtggaggccc acatgccacc cactaccggg gcacgtggta cctgacgggc    1080
atcgtcagct ggggccaggg ctgcgcaacc gtgggccact ttggggtgta caccagggtc    1140
tcccagtaca tcgagtggct gcaaaagctc atgcgctcag agccacgccc aggagtcctc    1200
ctgcgagccc catttcccga caaaactcac acgtgcccgc cgtgcccagc tccggaactg    1260
ctgggcggac cgtcagtctt cctcttcccc ccaaaaccca aggacaccct catgatctcc    1320
cggacccctg aggtcacatg cgtggtggtg gacgtgagcc acgaagaccc tgaggtcaag    1380
ttcaactggt acgtggacgg cgtggaggtg cataatgcca agacaaagcc gcgggaggag    1440
cagtacaaca gcacgtaccg tgtggtcagc gtcctcaccg tcctgcacca ggactggctg    1500
aatggcaagg agtacaatgt caaggtctcc aacaaagccc tcccagcccc catcgagaa    1560
aaccatctcc aaagccaaag gcagccccg agaaccacag tgtacaccc tgcccccatc    1620
ccgggatgag ctgaccaaga accaggtcag cctgacctgc ctggtcaaag gcttctatcc    1680
cagcgacatc gccgtggagt gggagagcaa tgggcagccg gagaacaact acaagaccac    1740
gcctcccgtg ttggactccg acggctcctt cttcctctac agcaagctca ccgtggacaa    1800
gagcaggtgg cagcagggga acgtcttctc atgctccgtg atgcatgagg ctctgcacaa    1860
ccactacacg cagaagagcc tctccctgtc tccgggtaaa                        1900
```

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic linker peptide
<220> FEATURE:
<221> NAME/KEY: REPEAT
<222> LOCATION: (1)..(30)
<223> OTHER INFORMATION: This peptide may encompass 3 to 30 residues as -continued specified in the application

<400> SEQUENCE: 5

Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 6

Gly Gly Gly
1

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 7

Ser Gly Gly Ser Gly Gly Ser
1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 8

Gly Gly Ser Gly Gly Ser Gly Gly Ser Gly Gly Ser Gly Gly Gly
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 9

Gly Gly Ser Gly Gly Ser Gly Gly Ser Gly Gly Ser Gly Gly Ser Gly
1               5                   10                  15

Gly Ser

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctggctagc caccatgga                                              19

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cttgtcatcg tcgtccttgt agtcgtcacc agtggaacct ggaac         45

<210> SEQ ID NO 12
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gactacaagg acgacgatga caaggacaaa actcacacat gcccaccgtg cccagctccg    60
gaactcc                                                              67

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tagtggatcc tcatttaccc g                                              21

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtaagcttg ccatggagct gaggccctgg ttgc                                34

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gttttcaatc tctaggaccc actcgcc                                        27

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gccaggccac atgactactc cgc                                            23

```
<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggtgaattct cactcaggca ggtgtgaggg cagc                              34

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctacctgca ggccaccatg gtctcccagg ccctcagg                          38

<210> SEQ ID NO 19
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagttccgga gctgggcacg gcgggcacgt gtgagttttg tcgggaaatg g           51

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttactgcaga aggttatgca gcgcgtgaac atg                               33

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tttttcgaat tcagtgagct ttgttttttc cttaatcc                          38

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Tyr Lys Asp Asp Asp Asp Lys
1               5
```

<210> SEQ ID NO 23
<211> LENGTH: 696
<212> TYPE: PRT
<213> ORGANISM: Artificial Sequence
<220> FEATURE:
<223> OTHER INFORMATION: Description of Artificial Sequence: Synthetic amino acid construct

<400> SEQUENCE: 23

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365
```

Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Glu Phe Ala
    450                 455                 460

Gly Ala Ala Val Asp Lys Thr His Thr Cys Pro Pro Cys Pro Ala
465                 470                 475                 480

Pro Glu Leu Leu Gly Gly Pro Ser Val Phe Leu Phe Pro Pro Lys Pro
                485                 490                 495

Lys Asp Thr Leu Met Ile Ser Arg Thr Pro Glu Val Thr Cys Val Val
                500                 505                 510

Val Asp Val Ser His Glu Asp Pro Glu Val Lys Phe Asn Trp Tyr Val
            515                 520                 525

Asp Gly Val Glu Val His Asn Ala Lys Thr Lys Pro Arg Glu Glu Gln
        530                 535                 540

Tyr Asn Ser Thr Tyr Arg Val Val Ser Val Leu Thr Val Leu His Gln
545                 550                 555                 560

Asp Trp Leu Asn Gly Lys Glu Tyr Lys Cys Lys Val Ser Asn Lys Ala
                565                 570                 575

Leu Pro Ala Pro Ile Glu Lys Thr Ile Ser Lys Ala Lys Gly Gln Pro
            580                 585                 590

Arg Glu Pro Gln Val Tyr Thr Leu Pro Pro Ser Arg Asp Glu Leu Thr
        595                 600                 605

Lys Asn Gln Val Ser Leu Thr Cys Leu Val Lys Gly Phe Tyr Pro Ser
    610                 615                 620

Asp Ile Ala Val Glu Trp Glu Ser Asn Gly Gln Pro Glu Asn Asn Tyr
625                 630                 635                 640

Lys Thr Thr Pro Pro Val Leu Asp Ser Asp Gly Ser Phe Phe Leu Tyr
                645                 650                 655

Ser Lys Leu Thr Val Asp Lys Ser Arg Trp Gln Gln Gly Asn Val Phe
                660                 665                 670

Ser Cys Ser Val Met His Glu Ala Leu His Asn His Tyr Thr Gln Lys
            675                 680                 685

Ser Leu Ser Leu Ser Pro Gly Lys
        690                 695

<210> SEQ ID NO 24
<211> LENGTH: 2091
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 24
atgcagcgcg tgaacatgat catggcagaa tcaccaggcc tcatcaccat ctgccttta      60 ggatatctac tcagtgctga atgtacagtt tttcttgatc atgaaaacgc caacaaaatt     120
ctgaatcggc caaagaggta taattcaggt aaattggaag agtttgttca agggaacctt    180

| | |
|---|---|
| gagagagaat gtatggaaga aaagtgtagt tttgaagaag cacgagaagt ttttgaaaac | 240 |
| actgaaagaa caactgaatt ttggaagcag tatgttgatg gagatcagtg tgagtccaat | 300 |
| ccatgtttaa atggcggcag ttgcaaggat gacattaatt cctatgaatg ttggtgtccc | 360 |
| tttggatttg aaggaaagaa ctgtgaatta gatgtaacat gtaacattaa gaatggcaga | 420 |
| tgcgagcagt tttgtaaaaa tagtgctgat aacaaggtgg tttgctcctg tactgaggga | 480 |
| tatcgacttg cagaaaacca gaagtcctgt gaaccagcag tgccatttcc atgtggaaga | 540 |
| gtttctgttt cacaaacttc taagctcacc cgtgctgaga ctgttttttcc tgatgtggac | 600 |
| tatgtaaatt ctactgaagc tgaaaccatt ttggataaca tcactcaaag cacccaatca | 660 |
| tttaatgact tcactcgggt tgttggtgga aagatgccaa accaggtca attcccttgg | 720 |
| caggttgttt tgaatggtaa agttgatgca ttctgtggag gctctatcgt taatgaaaaa | 780 |
| tggattgtaa ctgctgccca ctgtgttgaa actggtgtta aaattacagt tgtcgcaggt | 840 |
| gaacataata ttgaggagac agaacataca gagcaaaagc gaaatgtgat tcgaattatt | 900 |
| cctcaccaca actacaatgc agctattaat aagtacaacc atgacattgc ccttctggaa | 960 |
| ctggacgaac cctagtgct aaacagctac gttacaccta tttgcattgc tgacaaggaa | 1020 |
| tacacgaaca tcttcctcaa atttggatct ggctatgtaa gtggctgggg aagagtcttc | 1080 |
| cacaaaggga gatcagcttt agttcttcag taccttagag ttccacttgt tgaccgagcc | 1140 |
| acatgtcttc gatctacaaa gttcaccatc tataacaaca tgttctgtgc tggcttccat | 1200 |
| gaaggaggta gagattcatg tcaaggagat agtgggggac cccatgttac tgaagtggaa | 1260 |
| gggaccagtt tcttaactgg aattattagc tggggtgaag agtgtgcaat gaaaggcaaa | 1320 |
| tatggaatat ataccaaggt atcccggtat gtcaactgga ttaaggaaaa aacaaagctc | 1380 |
| actgaattcg ccggcgccgc tgcggtcgac aaaactcaca catgcccacc gtgcccagca | 1440 |
| cctgaactcc tggggggacc gtcagtcttc ctcttccccc caaaacccaa ggacaccctc | 1500 |
| atgatctccc ggacccctga ggtcacatgc gtggtggtgg acgtgagcca cgaagaccct | 1560 |
| gaggtcaagt tcaactggta cgtggacggc gtggaggtgc ataatgccaa gacaaagccg | 1620 |
| cgggaggagc agtacaacag cacgtaccgt gtggtcagcg tcctcaccgt cctgcaccag | 1680 |
| gactggctga atggcaagga gtacaagtgc aaggtctcca acaaagccct cccagccccc | 1740 |
| atcgagaaaa ccatctccaa agccaaaggg cagccccgag aaccacaggt gtacaccctg | 1800 |
| cccccatccc gggatgagct gaccaagaac caggtcagcc tgacctgcct ggtcaaaggc | 1860 |
| ttctatccca gcgacatcgc cgtggagtgg gagagcaatg ggcagccgga gaacaactac | 1920 |
| aagaccacgc ctcccgtgtt ggactccgac ggctccttct tcctctacag caagctcacc | 1980 |
| gtggacaaga gcaggtggca gcaggggaac gtcttctcat gctccgtgat gcatgaggct | 2040 |
| ctgcacaacc actacacgca gaagagcctc tccctgtctc cgggtaaatg a | 2091 |

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Pro Lys Asn Ser Ser Met Ile Ser Asn Thr Pro
1               5                   10

<210> SEQ ID NO 26

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Gln Ser Leu Gly Thr Gln
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Gln Asn Leu Ser Asp Gly Lys
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Gln Asn Ile Ser Asp Gly Lys
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Ile Ser Ser His Leu Gly Gln
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide
<220> FEATURE:
<221> NAME/KEY: REPEAT
<222> LOCATION: (1)..(10)
<223> OTHER INFORMATION: This peptide may encompass 1 to 10 residues as
      specified in the application

<400> SEQUENCE: 30

Gly Gly Gly Gly Gly Gly Gly Gly Gly Gly
1               5                   10

<210> SEQ ID NO 31
<211> LENGTH: 50
<212> TYPE: PRT
<213> ORGANISM: Artificial Sequence
<220> FEATURE:
<223> OTHER INFORMATION: Description of Artificial Sequence: Synthetic
```

```
        linker peptide
<220> FEATURE:
<221> NAME/KEY: REPEAT
<222> LOCATION: (1)..(50)
<223> OTHER INFORMATION: This peptide may encompass 5 to 50 residues as
      specified in the application

<400> SEQUENCE: 31

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 32
<211> LENGTH: 4
<212> TYPE: PRT
<213> ORGANISM: Artificial Sequence
<220> FEATURE:
<223> OTHER INFORMATION: synthetic peptide

<400> SEQUENCE: 32

Glu Leu Leu Gly
1
```